US012616666B2

(12) United States Patent
Narain et al.

(10) Patent No.: US 12,616,666 B2
(45) **Date of Patent: *May 5, 2026**

(54) COENZYME Q10 FORMULATIONS IN THE TREATMENT AND PREVENTION OF EPIDERMOLYSIS BULLOSA

(71) Applicant: BPGbio, Inc., Framingham, MA (US)

(72) Inventors: Niven Rajin Narain, Cambridge, MA (US); Rangaprasad Sarangarajan, Boylston, MA (US); Michael Andrew Kiebish, Millis, MA (US)

(73) Assignee: BPGbio, Inc., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/863,964

(22) Filed: Jul. 13, 2022

(65) Prior Publication Data

US 2023/0142060 A1 May 11, 2023

Related U.S. Application Data

(63) Continuation of application No. 15/981,831, filed on May 16, 2018, now Pat. No. 11,419,830.

(60) Provisional application No. 62/507,773, filed on May 17, 2017.

(51) Int. Cl.

| | |
|---|---|
| ***A61P 17/02*** | (2006.01) |
| ***A61K 31/122*** | (2006.01) |
| ***A61K 31/513*** | (2006.01) |
| ***A61K 39/395*** | (2006.01) |
| ***A61K 45/06*** | (2006.01) |
| *A61K 9/00* | (2006.01) |
| *A61K 9/06* | (2006.01) |
| *A61Q 19/00* | (2006.01) |

(52) U.S. Cl.

CPC .......... *A61K 31/122* (2013.01); *A61K 31/513* (2013.01); *A61K 39/395* (2013.01); *A61K 45/06* (2013.01); *A61P 17/02* (2018.01); *A61K 9/0014* (2013.01); *A61K 9/06* (2013.01); *A61Q 19/007* (2013.01)

(58) Field of Classification Search

None

See application file for complete search history.

(56) References Cited

U.S. PATENT DOCUMENTS

| | | | | |
|---|---|---|---|---|
| 4,636,381 | A | 1/1987 | Takada et al. | |
| 4,895,727 | A | 1/1990 | Allen | |
| 5,863,556 | A | 1/1999 | Ruckert et al. | |
| 5,891,469 | A | 4/1999 | Amselem | |
| 5,989,583 | A | 11/1999 | Amselem | |
| 6,048,846 | A | 4/2000 | Cochran | |
| 6,312,720 | B1 | 11/2001 | Katinger et al. | |
| 6,348,506 | B2 | 2/2002 | Sneed | |
| 6,465,517 | B1 | 10/2002 | Van Der Zee | |
| 6,569,463 | B2 | 5/2003 | Patel et al. | |
| 6,726,924 | B2 | 4/2004 | Keller | |
| 6,753,325 | B2 | 6/2004 | Rosenbloom | |
| 6,764,693 | B1 | 7/2004 | Smith | |
| 6,923,988 | B2 | 8/2005 | Patel et al. | |
| 7,005,274 | B1 | 2/2006 | Terkeltaub et al. | |
| 7,060,733 | B2 | 6/2006 | Pandol et al. | |
| 7,273,606 | B2 | 9/2007 | Fantuzzi et al. | |
| 10,583,098 | B2 * | 3/2020 | Hsia | A61P 21/00 |
| 11,419,830 | B2 | 8/2022 | Narain et al. | |
| 2002/0034537 | A1 | 3/2002 | Schulze et al. | |
| 2002/0039595 | A1 | 4/2002 | Keller | |
| 2002/0048551 | A1 | 4/2002 | Keller et al. | |
| 2002/0058712 | A1 | 5/2002 | Sneed | |
| 2002/0136711 | A1 | 9/2002 | Cochran | |
| 2002/0156062 | A1 | 10/2002 | Boch et al. | |
| 2002/0198177 | A1 | 12/2002 | Horrobin | |
| 2003/0103954 | A1 | 6/2003 | Rosenbloom | |
| 2003/0105027 | A1 | 6/2003 | Rosenbloom | |
| 2003/0105031 | A1 | 6/2003 | Rosenbloom | |
| 2003/0118536 | A1 | 6/2003 | Rosenbloom | |
| 2003/0232033 | A1 | 12/2003 | Cantrell | |
| 2003/0236239 | A1 | 12/2003 | Brancato et al. | |
| 2004/0034107 | A1 | 2/2004 | Enzmann | |
| 2004/0037828 | A1 | 2/2004 | Tennenbaum et al. | |
| 2004/0063661 | A1 | 4/2004 | Linnane | |
| 2004/0115181 | A1 | 6/2004 | Fujii et al. | |
| 2004/0170625 | A1 | 9/2004 | Goldstein et al. | |
| 2004/0247658 | A1 | 12/2004 | Trubiano et al. | |
| 2005/0019268 | A1 | 1/2005 | Enzmann | |
| 2005/0025756 | A1 | 2/2005 | Erwin | |
| 2005/0070610 | A1 | 3/2005 | Fujii et al. | |
| 2005/0084505 | A1 | 4/2005 | Muller et al. | |

(Continued)

FOREIGN PATENT DOCUMENTS

| | | |
|---|---|---|
| CN | 102548549 A | 7/2012 |
| CN | 104507308 A | 4/2015 |

(Continued)

OTHER PUBLICATIONS

Fine et al. J Am Acad Dermatol, Jun. 2008, pp. 931-950.*
Knott et al. International Union of Biochemistry and Molecular Biology, 2015, 41(6), pp. 383-390.*
Barlow, HPN introduces its new editorial board. Healthcare Purchasing News. Retrived online at: http://www.hpnonline.com/inside/december04.html. 6 pages, Dec. 2004.
Fine et al., The classification of inherited epidermolysis bullosa (EB): Report of the Third International Consensus Meeting on Diagnosis and Classification of EB. J Am Acad Dermatol. Jun. 2008;58(6):931-50.
Ikotyosa, Disease Name: Epidermolysis Bullosa. Japanese Society of Pediatrics. Retrieved online at: http://www.jpeds.or.jp/uploads/files/2016_ikotyosa_hokoku-143-144.pdf. pp. 143-144, (2016).
Johnson et al., Partial-thickness burns: identification and management. Adv Skin Wound Care. Jul.-Aug. 2003;16(4):178-87; quiz 188-9.

(Continued)

*Primary Examiner* — Vera Afremova
(74) *Attorney, Agent, or Firm* — McCarter & English, LLP; Jill Mello

(57) ABSTRACT

The present invention is directed, in part, to methods of treating Epidermolysis Bullosa (EB) in a subject in need thereof, comprising topical administration of a pharmaceutical composition comprising a therapeutically effective amount of a of Coenzyme Q10 (CoQ10) to the subject.

10 Claims, 20 Drawing Sheets

(56) References Cited

U.S. PATENT DOCUMENTS

| | | | |
|---|---|---|---|
| 2005/0208118 A1 | 9/2005 | Takemoto | |
| 2005/0239721 A1 | 10/2005 | Rosenbloom | |
| 2006/0110415 A1 | 5/2006 | Gupta | |
| 2006/0251708 A1 | 11/2006 | Chen et al. | |
| 2007/0009583 A1 | 1/2007 | Qvist | |
| 2007/0026072 A1 | 2/2007 | Olsen et al. | |
| 2008/0175935 A1* | 7/2008 | Kern | A61Q 19/08 424/773 |
| 2009/0098201 A1 | 4/2009 | Smith | |
| 2011/0064747 A1 | 3/2011 | Sarangarajan et al. | |
| 2012/0231038 A1 | 9/2012 | Trexler et al. | |
| 2013/0266557 A1 | 10/2013 | Sarangarajan et al. | |
| 2013/0323335 A1 | 12/2013 | Rozenblat et al. | |
| 2021/0000761 A1 | 1/2021 | Hsia et al. | |

FOREIGN PATENT DOCUMENTS

| | | | |
|---|---|---|---|
| DE | 19905879 | A1 | 8/2000 |
| EP | 0069399 | A2 | 1/1983 |
| EP | 0261362 | A3 | 5/1989 |
| EP | 1588703 | A4 | 6/2008 |
| EP | 1281398 | B1 | 7/2008 |
| JP | S62-077318 | A | 4/1987 |
| JP | 2004-531468 | A | 10/2004 |
| JP | 2007-063160 | A | 3/2007 |
| JP | 2007-518805 | A | 7/2007 |
| JP | 2009-040757 | A | 2/2009 |
| JP | 2009-191039 | A | 8/2009 |
| JP | 2009-536215 | A | 10/2009 |
| JP | 2013-503175 | A | 1/2013 |
| JP | 2015-518056 | A | 6/2015 |
| WO | WO-2000/57871 | A2 | 10/2000 |
| WO | WO-2005/069916 | A1 | 10/2006 |
| WO | WO-2007/131047 | A2 | 11/2007 |
| WO | WO-2013/181639 | A1 | 12/2013 |
| WO | WO-2017/066552 | A1 | 4/2017 |

OTHER PUBLICATIONS

Ogura et al., Effect of CoQ10 Liposome Lotion on Lipid Peroxidation in the Epidermis Exposed to Ultraviolet Light. Journal of the Kurume Medical Association. 1986;49(1):64-69.

Playford et al., Combined effect of coenzyme Q10 and fenofibrate on forearm microcirculatory function in type 2 diabetes. Atherosclerosis. May 2003;168(1):169-79.

Pope et al., Epidermolysis bullosa and chronic wounds: a model for wound bed preparation of fragile skin. Adv Skin Wound Care. Apr. 2013;26(4):177-88.

Sahlin et al., Energy supply and muscle fatigue in humans. Acta Physiol Scand. Mar. 1998;162(3):261-6.

Schober-Flores, Epidermolysis Bullosa: The Challenges of Wound Care. Dermatology Nursing. 2003;15(2):1-16.

International Search Report for Application No. PCT/US2007/068052, dated Apr. 15, 2008.

International Search Report and Written Opinion for Application No. PCT/US2018/033046, dated Jul. 24, 2018, 11 pages.

* cited by examiner

CoEnzyme Q10 Concentration (μM)

Prior Art

Prior Art

Figure 1: Week 1, Day 1 photograph of medial lower left leg

Figure 2: Week 2 photograph of medial lower left leg

Fig. 13 A-D
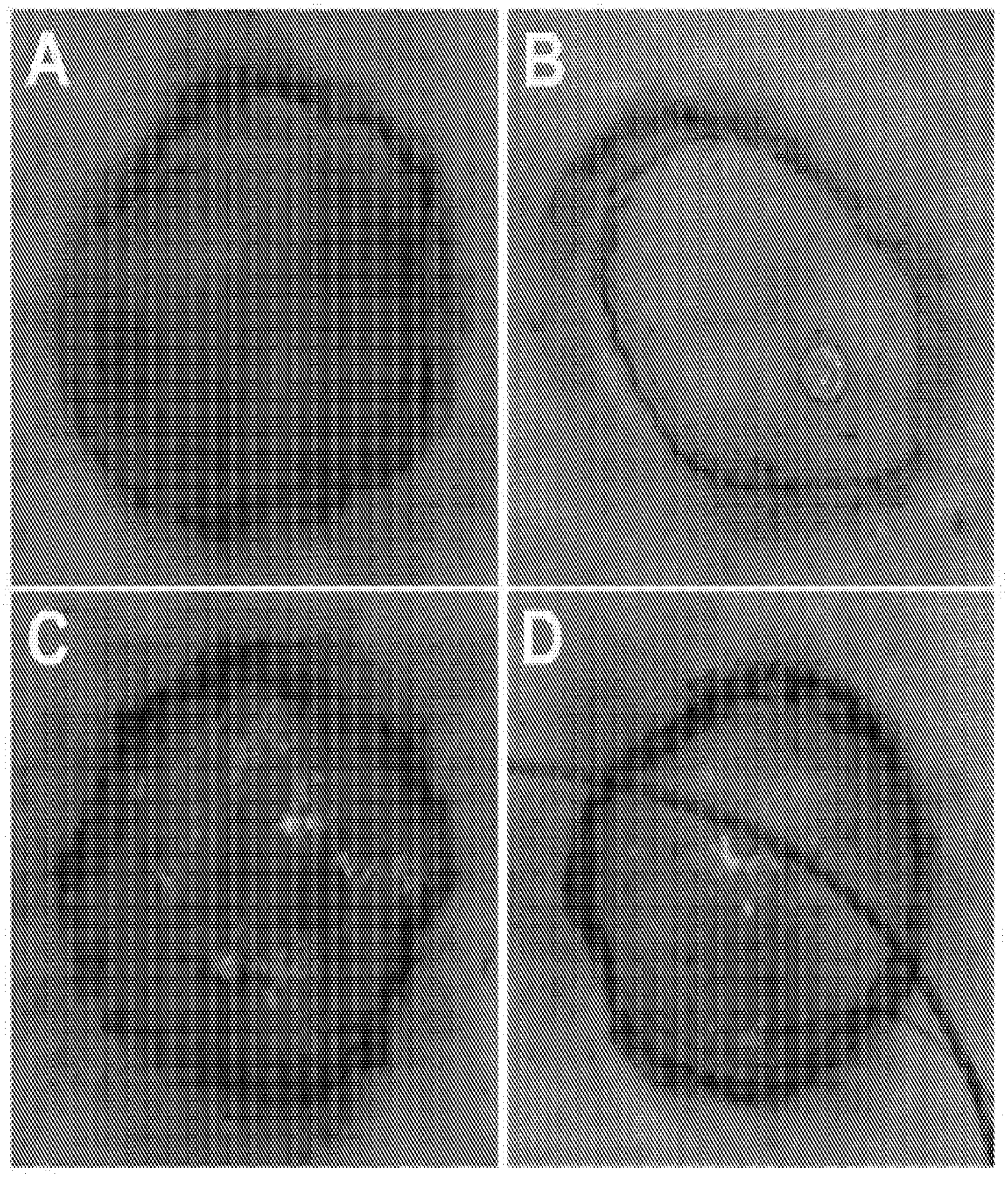

COENZYME Q10 FORMULATIONS IN THE TREATMENT AND PREVENTION OF EPIDERMOLYSIS BULLOSA

RELATED APPLICATIONS

This application is a continuation application of U.S. application Ser. No. 15/981,831, filed May 16, 2018, allowed, which, in turn, claims priority to U.S. Provisional Application No. 62/507,773 filed on May 17, 2017, the entire contents of which is incorporated by reference in its entirety herein.

BACKGROUND OF THE INVENTION

According to the Dystrophic Epidermolysis Bullosa Research Association (DebRA), 1 out of every 50,000 babies born are affected with Epidermolysis Bullosa (EB). This is seen across all racial and ethnic groups, and in both sexes equally worldwide. EB comprises a group of genetically determined skin fragility disorders characterized by blistering or tearing of the skin and mucosae following mild mechanical trauma. Traditionally, it was asserted that there were three major groups of inherited EB, namely EB simplex, junctional EB and dystrophic EB; based on the ultrastructural level within which skin cleaves and blisters. (Pearson, R. W., 1988). In 2007, the third international consensus meeting on diagnosis and classification of EB was held in Vienna, Austria. Based on the outcome of this meeting, EB is now classified into 4 major types; mixed type (Kindler syndrome) being the fourth major type. Availability of monoclonal and polyclonal antibodies coupled with advances in molecular diagnostic techniques have led to the sub-classification of EB into at least 30 different subtypes (Fine J D 2010).

One hallmark of these conditions is the formation of blisters or wounds which are caused by minor mechanical trauma, friction or heat, with the severity of the disease dependent on the type of EB present. Individuals with EB have significantly delayed healing for the blisters and/or wounds, which are prone to infections. All forms of EB simplex (EBS) have sites that tend to be fragile with a tendency to break and form a lesion within the epidermis (Hanna, Silverman, Boxall, Krafchik, 1983), and generally begin with the disruption of basal keratinocytes. EBS is usually dominantly inherited, and involves disorders of the genes coding keratins 5, 14 and plectin. In rare forms of EBS, there may also be plectin mutations and a likelihood of muscular dystrophy. In contrast, junctional and dystrophic forms of EB are the result of structural breaks within or near the basement membrane zone. In junctional EB (JEB), skin cleavage uniformly develops within the lamina lucida, the narrow electron-sparse upper half of the dermo-epidermal junction. JEB is a recessively inherited disease and involves many genes for components between the epidermis and dermis such as laminin 332, plectin and a6b4-integrin. In dystrophic EB (DEB), cleavage always occurs between the levels of the lamina densa, which is the electrondense lower half of the dermo-epidermal junction (upper dermis). (Fine J D., Schachner L A, 1995). Kindler syndrome accounts for about 1% of EB patients, and involves all layers of the skin having extreme fragility.

EB phenotypes are further sub-classified on the basis of the extent of cutaneous involvement (localized versus generalized), the specific nature of the regional distribution of lesions; the types of morphologic lesions present on the skin; the extent (if present) and diversity of extracutaneous disease activity; and the mode of inheritance (autosomal dominant, autosomal recessive). All forms of EB are characterized by a lifetime of recurrent blister and/or wound formation, which linger and often become infected. Blisters can form anywhere on the surface of the skin, including within the oral cavity, surfaces of the eye, in the respiratory tract, gastrointestinal tract and/or the genitourinary tract. In addition to the chronic blisters and wounds, disfiguring scars and disabling musculoskeletal deformities can occur.

Some forms of EB are associated with normal longevity. However, several forms of severe EB experience profound morbidity and markedly increased mortality as either a direct or indirect result of the EB. Many people with EB become anemic due to chronic loss of blood through wounds, poor nutritional intake, poor absorption of iron and bone marrow suppression from chronic inflammation. Other patients have selenium and carnitine or vitamin D deficiencies which make them prone to osteoporosis and/or cardiomyopathy. Death often occurs during the first three decades in severely affected patients. Repeated infections in the already nutritionally compromised, anemic patient are usually the cause. Another serious complication in both the dystrophic form and junctional form of EB is the development of aggressive squamous cell carcinomas during young adulthood. Most patients die as the result of widespread metastatic disease, regardless of how early and how aggressively the primary tumors were diagnosed and treated. Tracheolaryngeal obstruction is also a risk for a minority of patients with all forms of junctional EB.

Cutaneous involvement (wounds) can range from blisters on the extremities to more generalized wounds throughout the body. Wounds can occur as a single lesion or can be a cluster depending on the location and/or cause of the injury. The lesions in EB patients have a tendency to expand if left untreated, and not heal. Typical wound healing (in people not affected by EB) is an orchestrated serial process of predictable events of tissue repair involving immune cells, platelets, keratinocytes, fibroblasts and macrophages playing essential roles. (Demidova-Rice, et al., 2012). There are two major types of DEB, one being dominant and the other recessive, and both involve defects in type VII collagen. The genetic aberrations in the skin of patients with EB leads to life-long skin problems which can never resolve, and which significantly negatively impact quality of life.

In contrast to normal wound healing, chronic wounds such as those observed in patients with EB, demonstrate a persistent, exaggerated inflammatory phase, without progression into the healing phases. (Schober-Flores C., 2003). As a result of the prolonged, chronic nature of these wounds, they are prone to persistent infections. Patients with EB suffer from pain and discomfort, battle recurrent skin infections, are severely limited in their lifestyle choices, often suffer anemia, malnourishment, constipation, osteoporosis, cardiomyopathy, cancer, and other afflictions. Standard of care wound treatments cannot effectively treat EB patients as their skin lacks the proper expression of structural and functional proteins which prevent or repair damage from environmental factors (e.g., heat, humidity) and/or mechanical stress (e.g., friction, trauma), and there is no ability to cure EB as it is driven by genetic mutations of the patients' skin.

There is no specific proven treatment for any form of EB, and the mainstay of clinical management is based on wound care, pain management and avoidance of provoking factors. At the present time, treatment of inherited EB is essentially supportive. Good topical therapy is fundamental, consisting primarily of sterile dressings and topical antibiotics. Standard of care includes the use of antibiotics in creams or ointments covered with Vaseline-impregnated gauze or a non-adherent synthetic dressing. Vulnerable areas prone to repeat injury are protected with thick applications of tubular gauze. Such dressings are usually changed daily. Intermittent courses of systemic antibiotics are required when more than minor infection occurs.

Proper and adequate wound care remains the cornerstone for effective management irrespective of the type of EB diagnosis and form of lesions. Despite the availability of an extensive spectrum of wound care products for wounds in normal-healing skin, in the clinical setting, their utility for use in EB is extremely limited.

Accordingly, a significant need remains in the art for improved treatment options for EB in its various forms.

SUMMARY OF THE INVENTION

The present invention is based, at least in part, upon the surprising finding that topically applied Coenzyme Q10 (CoQ10) can be used to treat subjects with EB. Additionally, topically applied CoQ10 can structurally and functionally improve the integrity of the skin and the healing of wounds of the skin in patients with EB. Without being bound by theory, the present invention reports the surprising and unexpected finding that topical application of CoQ10 can promote the transition from the inflammation stage of healing (where EB blisters and/or wounds typically stagnate) into the proliferation and remodeling stages, thus allowing blisters and/or wounds to resolve. The present invention represents a new therapy to treat patients with EB.

In one embodiment of the invention, topical CoQ10 can be used to alter the expression of structural and/or functional proteins that are missing in EB patients, a correction of which may improve the structural integrity of the skin.

Another embodiment of the invention is a method of treating Epidermolysis Bullosa (EB) in a subject in need thereof, comprising topical administration of a pharmaceutical composition comprising a therapeutically effective amount of CoQ10 to the subject, wherein treatment of the subject results in the reduction of size of one or more blisters and/or wounds by at least about 70% after administration of an effective amount of CoQ10 for a treatment duration of about four weeks.

Another embodiment of the invention is a method of treating a wound associated with Epidermolysis Bullosa (EB) in a subject in need thereof, comprising topical administration of a pharmaceutical composition comprising a therapeutically effective amount of CoQ10 to the subject.

A further embodiment of the present invention is a method of improving the structural integrity of the skin of a subject suffering from Epidermolysis Bullosa, comprising topical administration of a pharmaceutical composition comprising a therapeutically effective amount of CoQ10 to the skin of the subject.

One embodiment of the invention is a method of increasing the rate of healing of a skin blister and/or wound in a subject suffering from EB, comprising topical administration of a pharmaceutical composition comprising a therapeutically effective amount of Coenzyme Q10 (CoQ10) to the skin blister and/or wound.

In another embodiment, the invention is a method of treating or preventing squamous cell carcinoma in a subject suffering from Epidermolysis Bullosa, comprising topical administration of a pharmaceutical composition comprising a therapeutically effective amount of CoQ10 to the subject.

In any of the above embodiments, the Epidermolysis Bullosa is Epidermolysis Bullosa Simplex, Junctional Epidermolysis Bullosa, Dystrophic Epidermolysis Bullosa, or Kindler's Syndrome.

In any of the above embodiments, the pharmaceutical composition comprising CoQ10 is applied to a blister and/or wound on the skin. In any of the above embodiments, the pharmaceutical composition comprising CoQ10 is applied to intact skin. In another embodiment, the topical pharmaceutical composition is a preparation selected from the group consisting of an ointment, cream, emulsion, lotion and gel. In one embodiment, the topical pharmaceutical composition is in the form of a cream. In one aspect of this embodiment, the topical pharmaceutical composition contains from about 1% to about 5% CoQ10 (w/w). In another aspect of this embodiment, the topical pharmaceutical composition contains about 3% CoQ10 (w/w).

In any of the above embodiments, topical administration of the CoQ10 pharmaceutical composition of the invention provides one or more beneficial effect to the subject suffering from EB after treatment with an effective amount of CoQ10. In some aspects of this embodiment, the one or more beneficial effect is selected from the group consisting of: reduction in pain associated with the EB; reduction in inflammation associated with the EB; reduction in the size of blisters and/or wounds associated with the EB; reduction in the number of blisters and/or wounds associated with the EB; increase in the rate of healing of one or more blisters and/or wounds associated with the EB; increase in the structural integrity of the skin of the subject suffering from EB; reduction in the number of skin infections associated with EB; increase in wound closure of wounds associated with EB; increase in re-epithelization of wounds associated with EB; increase in granulation of wounds associated with EB; reduction in an epidermal gap distance of a blister and/or wound associated with EB; reduction in time for blister and/or wound healing associated with EB; reduction in the amount of concomitant medications administered to the subject in order to treat the subject's EB; reduction in scarring associated with EB; increase in keratinocyte production in the skin of the subject; and increase in fibroblast production in the skin of the subject.

In one embodiment, administration of the composition comprising a therapeutically effective amount of CoQ10 decreases the time to healing of the blister and/or wound compared to an untreated blister and/or wound. In another embodiment, administration of the composition comprising a therapeutically effective amount of CoQ10 improves the quality of healing using the Epidermolysis Bullosa Disease Activity and Scarring Index (EBDASI) compared to an untreated blister and/or wound. In one embodiment, administration of the composition comprising a therapeutically effective amount of CoQ10 increases resistance to mechanical trauma of the skin compared to untreated skin. In one embodiment, administration of the composition comprising a therapeutically effective amount of CoQ10 reduces the formation of blisters and/or wounds of the skin compared to untreated skin. In another embodiment, the composition comprising CoQ10 is applied to a blister and/or wound on the skin. In another embodiment, the composition comprising CoQ10 is applied to intact skin.

In another aspect, the invention features a method of promoting healing of a skin blister and/or wound in a subject suffering from Epidermolysis Bullosa, comprising topical administration to the blister and/or wound of a composition comprising a therapeutically effective amount of Coenzyme Q10 (CoQ10), thereby promoting healing of the skin blister and/or wound in the subject. In one embodiment, the rate of re-epithelialization of the blister and/or wound treated with the CoQ10 composition is increased compared to the rate of re-epithelialization of an untreated blister and/or wound. In one embodiment, an epidermal gap distance of the blister and/or wound is reduced in comparison to an epidermal gap distance of an untreated blister and/or wound. In one embodiment, the quality of epidermal integrity of the blister and/or wound treated with the CoQ10 composition is improved compared to the quality of epidermal integrity of an untreated blister and/or wound. In another embodiment, the quality of epidermal integrity is assessed using histologic examinations of the blister roof. In one embodiment, the level of expression of one or more structural proteins in the blister and/or wound treated with the CoQ10 composition is modulated in comparison to the level of expression of the one or more structural proteins in an untreated blister and/or wound. In another embodiment, the one or more structural proteins is selected from the group consisting of a keratin, a collagen, a plectin, an annexin, a vimentin, a filamin and a laminin. In a further embodiment, the keratin is selected from the group consisting of keratin 13 (KRT13), keratin 14 (KRT14) and keratin 17 (KRT17). In a further embodiment, the protein is one or more protein selected from the group consisting of keratin 5, keratin 14, plectin, laminin 332, a6b4-integrin, and type VII collagen.

In another aspect, the invention features a method of treating a subject with Epidermolysis Bullosa, comprising administration to the subject of a composition comprising a therapeutically effective amount of CoQ10, thereby treating the subject. In one embodiment, the subject is identified as having an alteration in the expression of one or more structural proteins in the skin. In another embodiment, the one or more structural proteins is selected from the group consisting of a keratin, a collagen, a plectin, an annexin, a vimentin, a filamin and a laminin. In another embodiment, the keratin is selected from the group consisting of keratin 13 (KRT13), keratin 14 (KRT14) and keratin 17 (KRT17). In a further aspect of this embodiment, the protein is one or more protein selected from the group consisting of keratin 5, keratin 14, plectin, laminin 332, a6b4-integrin, and type VII collagen. In a further embodiment, the expression of one or more structural proteins results in increased fibroblasts and/or keratinocytes in the skin of the subject.

In another aspect, the invention features a method of treating or preventing squamous cell carcinoma in a subject suffering from Epidermolysis Bullosa, comprising topical administration of a composition comprising a therapeutically effective amount of CoQ10 to the subject, thereby treating or preventing squamous cell carcinoma in the subject. In one embodiment, the composition comprising CoQ10 is administered to squamous cell carcinoma cells in the subject. In one embodiment, the composition comprising CoQ10 is administered to an area of skin comprising squamous cell carcinoma cells in the subject. In one embodiment, the squamous cell carcinoma is cutaneous squamous cell carcinoma (cSCC). In one aspect of this embodiment, the composition of the invention is administered with an additional agent. In one aspect of this embodiment, the additional agent is a chemotherapeutic agent. In one aspect of this embodiment, the chemotherapeutic agent is cisplatin, doxorubicin, 5-fluorouracil, capecitabine, topotecan, or etoposide. In another aspect of this embodiment, the chemotherapeutic agent is 5-fluorouracil. In another aspect of this embodiment, the additional agent is diclofenac, imiquimod, or ingenol mebutate. In another aspect of this embodiment, the additional agent is a drug used in photodynamic therapy (PDT).

In one embodiment of the foregoing aspects, administration of the composition comprising CoQ10 modulates the expression of one or more proteins in the subject. In one embodiment, the protein is a stress protein or structural protein. In another further embodiment, the protein is selected from the group consisting of transaldolase 1, NM23 protein, heat shock 27 kDa protein 1, keratin 1, keratin 14, keratin 13, proteasome beta 7, proteasome activator subunit 3, and rho GDP dissociation inhibitor alpha. In another embodiment, the protein is selected from the group consisting of: V-akt murine thymoma viral oncogene homolog 1 (AKT1), BCL2-associated athanogene 4 (BAG4), BCL2-associated X protein (BAX), BCL2-like 1 (BCL2L1), BCL2/adenovirus E1B 19 kDa interacting protein 3 (BNIP3), caspase recruitment domain family, member 6 (CARD6), caspase 6, apoptosis-related cysteine peptidase (CASP6), caspase 7, apoptosis-related cysteine peptidase (CASP7), growth arrest and DNA-damage-inducible, alpha (GADD45A), tumor protein p53 (TP53) and tumor protein p73 (TP73).

In one embodiment of any of the above aspects or embodiments, the composition comprising CoQ10 comprises between 1% and 5% of Coenzyme Q10. In one embodiment, the composition comprising CoQ10 comprises about 1%, about 2%, about 3%, about 4% or about 5% of Coenzyme Q10. In one embodiment, the composition comprising CoQ10 comprises about 3% of Coenzyme Q10. In one embodiment of any of the above aspects or embodiments, the composition comprising CoQ10 is administered with a second composition comprising an additional agent. In one embodiment of any of the above aspects or embodiments, the composition comprising CoQ10 further comprises an additional agent. In one embodiment of any of the above aspects or embodiments, the composition comprising CoQ10 does not comprise any additional agent, i.e., Coenzyme Q10 is the sole active agent.

BRIEF DESCRIPTION OF THE DRAWINGS

FIG. 2A shows the results of a Western Blot for IDH-1 and a beta-actin loading control. FIG. 2B is a graph that shows the change in IDH-1 expression as a percent of control. As shown in FIG. 2B, treatment of SK-MEL-28 cells with Coenzyme Q10 is associated with a concentration dependent increase in expression of IDH-1.

FIG. 3A shows the results of a Western Blot for ACL and a beta-actin loading control. FIG. 3B is a graph that shows the change in ACL expression as a percent of control. As shown in FIG. 3A and FIG. 3B, treatment of SK-MEL-28 cells with Coenzyme Q10 is associated with a concentration dependent decrease in expression of ACL.

FIG. 4A shows the results of a Western Blot for p53, P14ARF and MDM2, and a beta-actin loading control. FIG. 4B is a graph that shows the change in p53, P14ARF and MDM2 expression as a percent of control.

FIGS. 13A-D show dermoscopy images taken 48 hours after wounding with a suction blister CELLUTOME system. Diffuse erythema is observed in non-treated wounds (13A, 13C), whereas small or none redness areas were present in treated wounds (13B, 13D).

DETAILED DESCRIPTION

Figure 1:
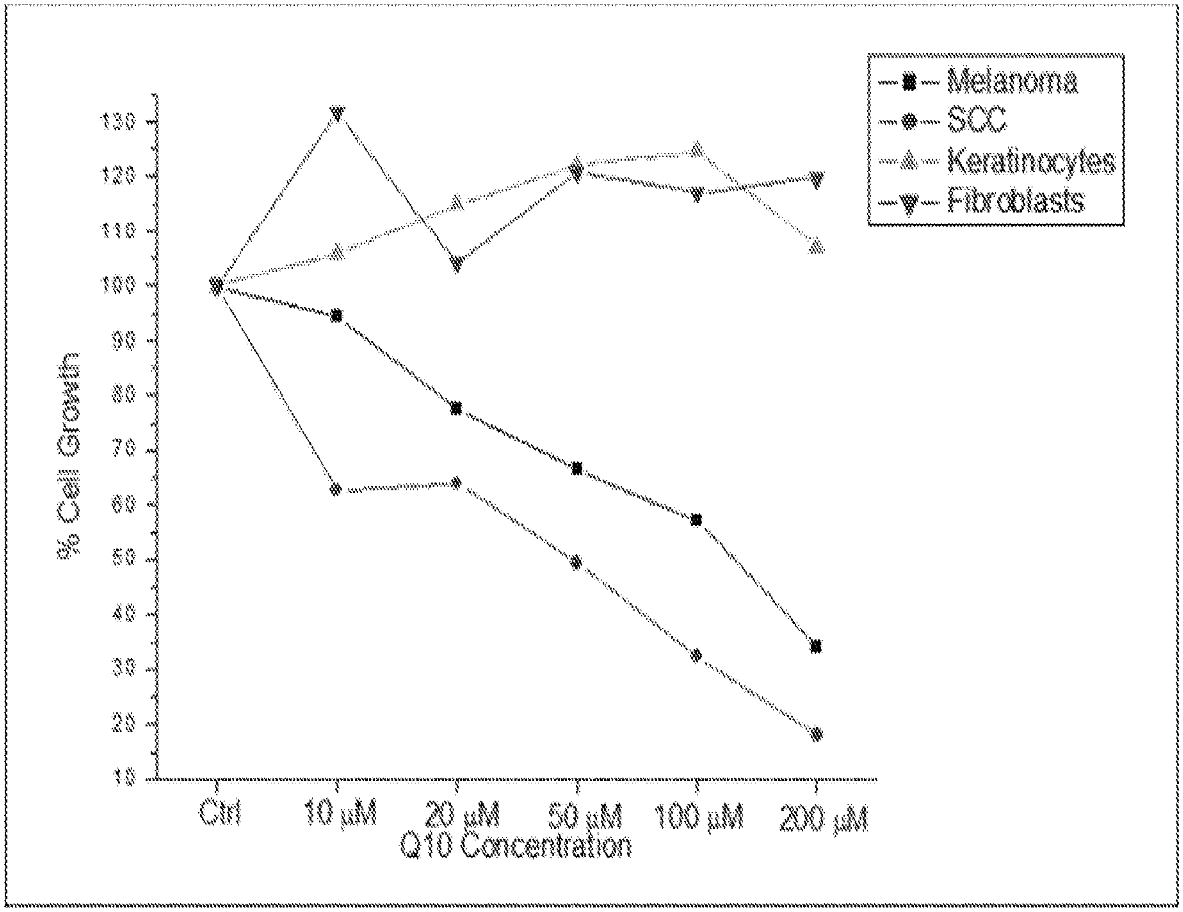
FIG. 1 is a graph that shows the effect of increasing concentration of Coenzyme Q10 exposure on the cell proliferation of cancer and normal cells.

Presently, there is no specific proven treatment for any form of EB. All types of EB are characterized by persistent blistering and wounding of the skin that require active management including the use of therapeutic modalities with the ability to repair and heal wounds. EB wounds are chronic, difficult to heal wounds that do not progress through typical phases associated with wound healing (Pope et al., 2013). Typical wounds progress through four stages of healing: 1) hemostasis, 2) inflammation, 3) proliferation, and 4) remodeling. (Guo, et. al, 2010). In EB, the inflammatory phase is often prolonged without progression through the next healing phases. The proliferative phase can be impaired due to reduced metabolic activity caused by infection, malnutrition, and tissue oxygenation status, and also by medications typically used for symptomatic treatment of the disease such as corticosteroids (Marinkovich et al, 2014). Remodeling in EB can also be impaired which results in abnormal wound contraction causing severe scarring. Targeting mitochondrial function in major cell types such as keratinocytes, fibroblasts, and endothelial cells associated with wound closure and healing has been suggested to be an important mechanism to effectuate improved wound healing. Mitochondrial metabolism provides energy for wound repair, regulates keratinocyte differentiation via production of reactive oxygen species and influences expression of genes central to the process of wound healing. (Feichtinger, et. al, 2014).

The present invention is based upon the surprising finding that topically applied Coenzyme Q10 can be used to treat patients suffering from EB. In one embodiment, topically applied Coenzyme Q10 can be used to treat skin blistering and/or wounds in patients with EB. Patients with EB are characterized by defects and/or deficiencies in the expression and/or activity of structural and functional proteins of the skin. In particular, in certain embodiments, the present invention provides methods of treatment of a particular population of EB subjects that have an alteration in expression of one or more structural proteins in the skin, e.g. keratins, collagens, plectin, annexins, vimentin, filamins, integrins and laminins. Because the skin of subjects with EB is compromised in the expression and/or activity of these structural proteins, the healing process of the wounds, e.g. skin blisters, is unique in subjects suffering from EB. In addition to the debilitating injuries to epithelial tissues in the various organs, patients with EB encounter other complications including growth retardation, anemia, muscular dystrophy and deformities of hands and feet. However, the cause of morbidity and mortality in adults with EB is related to the incidence of malignancies, of which cutaneous squamous cell carcinoma (cSCC) is most significant. The present invention also reports the surprising finding that topically applied Coenzyme Q10 (CoQ10) can be used to treat and/or prevent cSCC in patients with EB.

Topical administration of a pharmaceutical composition comprising Coenzyme Q10 of the present invention that has demonstrated to increase the expression of several structural proteins such as collagens, plectin, laminin, vimentin, annexin, KRT13, KRT14 and KRT17 in fibroblasts and keratinocytes. Also, topical application of CoQ10 has shown to block the upregulation of inflammatory cytokines (IL6) and decrease proliferation of SCC cells.

1. Definitions

Unless otherwise indicated, all terms used herein have the meanings given below, and are generally consistent with same meaning that the terms have to those skilled in the art of the present invention. Practitioners are particularly directed to Sambrook et al. (1989) Molecular Cloning: A Laboratory Manual (Second Edition), Cold Spring Harbor Press, Plainview, N.Y. and Ausubel F M et al. (1993) Current Protocols in Molecular Biology, John Wiley & Sons, New York, N.Y., for definitions and terms of the art. It is to be understood that this invention is not limited to the particular methodology, protocols, and reagents described, as these may vary.

The articles "a" and "an" are used herein to refer to one or to more than one (i.e. to at least one) of the grammatical object of the article.

The term "including" is used herein to mean, and is used interchangeably with, the phrase "including but not limited to".

The term "or" is used herein to mean, and is used interchangeably with, the term "and/or," unless context clearly indicates otherwise.

As used herein, the term "subject" can mean either a human or non-human animal, preferably a mammal. In preferred embodiments, the subjects are human.

As used herein, the term "agent" or "additional agent" means a compound or composition which may be useful to treat Epidermolysis Bullosa and/or a condition or symptom associated with EB, such as pain, inflammation, blood loss, wound healing, and the like. "Agents" and "additional agents" may further include treatments of diseases and disorders associated with EB, such as squamous cell carcinoma (SCC), anemia, and the like.

As used herein, the terms "treatment", "treating", and the like are used herein to generally mean improvement in any symptoms associated with or caused by EB. "Treatment", as used herein, may refer to a subject experiencing one or more of the following after administration of the CoQ10 composition: decrease in pain associated with EB, decrease in inflammation associated with EB, decrease in blister and/or wound formation, increase in rate of healing of blisters and/or wounds, increase in the rate of wound closure, increase in skin integrity (i.e., decrease in likelihood of tearing or blistering due to mechanical or environmental stress), decrease in the number of chronic blisters and/or wounds, decrease in the number of concomitant medications required to control EB symptoms, and decrease in the number of blisters and/or wounds which become infected, among others. Improvements in any of these symptoms can be readily assessed according to standard methods and techniques known in the art. The population of subjects treated by the method of the disease includes subjects suffering from any form of EB. As EB is a genetic condition, "treating" does not include curative measures.

As used herein, the term "preventing" is used herein to refer to preventing in whole or in part, or slowing the onset or progression of a disease or disorder. As used herein, preventing is meant to refer to accomplishing one or more of the following: (a) decreasing or slowing rate of progression of the severity of the disease or disorder; and (b) preventing or delaying development of the disease or disorder, as compared to the average time to onset of the sub-population of EB patients generally.

As used herein, the term "treatment duration" is used herein to refer to the amount of time which a subject administers the CoQ10 composition to a particular blister, wound and/or intact skin. Treatment duration should be as long as is required for the blister and/or wound to heal and resolve. Typically, the treatment duration will last from about 1 to about 12 weeks, but it may be longer for particular blisters and/or wounds. As EB is a genetic condition for which there is no cure, and a subject suffering from EB may have new blisters and/or wounds appear at any time, any of which may be chronic if treated with standard of care modalities. It is envisioned that a subject may have multiple blisters and/or wounds which require administration of the CoQ10 composition of the present invention at any given time, and that the start date of treatment and the end date of treatment may not coincide for each affected area. Additionally, for preventative uses, the treatment duration for administration of the CoQ10 composition of the present invention may not have a discreet endpoint, but will be determined by the physician overseeing the subject's treatment.

As used herein, the term a "therapeutically effective amount" in reference to the CoQ10 composition of the instant invention refers to the amount sufficient to induce a desired biological, pharmaceutical, or therapeutic result. That result can be alleviation of the signs or symptoms of a disease or disorder, or any other desired alteration of a biological system. In one embodiment of the present invention, the result will involve the promotion and/or improvement of blister and/or wound healing, including increasing the percentage of wound closure, shortening of the time to healing, improvement of the quality of healing, reduction in an epidermal gap distance and/or improvement of skin integrity.

As used herein, the term "skin blistering," "skin blister" or "blister" is meant to refer to a particular type of wound in the upper layers (epidermal layer and dermal layer) of the skin. In EB, one or more skin blisters may form when minor trauma, friction, or heat is applied to the skin.

As used herein, the term "wound" is meant to refer to an injury to living tissue caused by a cut, blow, or other impact, typically one in which the skin is cut or broken. Synonyms include "lesion", "tear", "gash", and/or "cleavage" of the skin.

Depending on the type of EB, skin blisters and/or wounds can form due to (1) skin cleavage within the basal layer of the epidermis, (2) skin and mucosal cleavage occurring at the lamina lucida level of the basement membrane zone, a critical interface between the epidermis and dermis and/or (3) cleavage beneath the lamina densa, within the dermis at the level of the anchoring fibrils. Any blister and/or wound can be acute or chronic.

As used herein, the term "intact skin" refers to skin in which there are no blisters and/or wounds. In certain embodiments, intact skin refers to skin in which there is no skin cleavage within the basal layer of the epidermis or skin in which there is no cleavage at the lamina lucida level of the basement membrane zone or skin in which there is no cleavage beneath the lamina densa.

As used herein, the term "structural protein" is meant to refer to a protein that maintains the epithelial integrity of the skin. In certain embodiments, the structural protein may be a keratin, a collagen, a plectin, an annexin, a vimentin, a filamin, an integrin and a laminin. In one embodiment, the structural protein of the invention is a protein for which a defect or deficiency is associated with, or causal of, Epidermolysis Bullosa.

As used herein, the term "functional protein" is meant to refer to a protein that has an activity that is integral to maintaining or re-establishing (e.g., healing) the integrity of the skin. In certain embodiments, the functional protein may be a keratin, a collagen, a plectin, an annexin, a vimentin, a filamin, an integrin and a laminin. In one embodiment, a functional protein of the invention is a protein for which a defect or deficiency is associated with, or causal of, Epidermolysis Bullosa.

The term "expression" as used herein is meant to refer to the process by which a polypeptide is produced from DNA. The process involves the transcription of the gene into mRNA and the translation of this mRNA into a polypeptide. Depending on the context in which used, "expression" may refer to the production of RNA, protein or both.

The terms "level of expression of a gene" or "gene expression level" is meant to refer to the level of mRNA, as well as pre-mRNA nascent transcript(s), transcript processing intermediates, mature mRNA(s) and degradation products, or the level of protein, encoded by the gene in the cell.

As used herein, the term "modulation" is meant to refer to upregulation (i.e., activation or stimulation) or downregulation (i.e., inhibition or suppression) of a response, or the two in combination or apart. A "modulator" is a compound or molecule that modulates, and may be, e.g., an agonist, antagonist, activator, stimulator, suppressor, or inhibitor.

As used herein, the term "alteration" is meant to refer to an increase or a decrease. In certain embodiments, an alteration refers to an increase or a decrease in protein expression. In other embodiments, an alteration refers to an increase or a decrease in gene expression.

Reference will now be made in detail to preferred embodiments of the invention. While the invention will be described in conjunction with the preferred embodiments, it will be understood that it is not intended to limit the invention to those preferred embodiments. To the contrary, it is intended to cover alternatives, modifications, and equivalents as may be included within the spirit and scope of the invention as defined by the appended claims.

2. Pharmaceutical Compositions and Pharmaceutical Administration

A. Coenzyme Q10

The terms "Coenzyme Q," and "CoQ10," are used interchangeably throughout the specification. CoQ10 has the following structure:

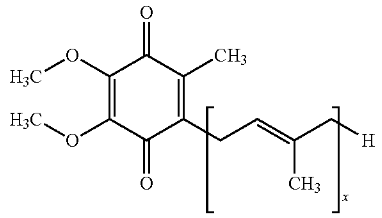

wherein x is 10. CoQ10 includes the fully oxidized version, also known as ubiquinone or ubidecarenone, the partially oxidized version, also known as semiquinone or ubisemiquinone, or the fully reduced version, also known as ubiquinol; or any mixtures or combinations thereof. In certain embodiments, the CoQ10 compound for use in the methods of the invention is ubidecarenone.

CoQ10 is art-recognized and further described in International Publication No. WO 2005/069916 (Appln. No. PCT/US2005/001581), WO 2008/116135 (Appln. No. PCT/US08/57786), WO2010/132507 (Appln. No. PCT/US2010/034453), WO 2011/112900 (Appln. No. PCT/US2011/028042), and WO2012/174559 (Appln. No. PCT/US2012/043001) the entire contents of each of which are expressly incorporated by reference herein. CoQ10 is one of a series of polyprenyl 2,3-dimethoxy-5-methylbenzoquinone (ubiquinone) present in the mitochondrial electron transport systems of eukaryotic cells. Human cells produce CoQ10 exclusively and it is found in cell and mitochondrial membranes of all human cells, with the highest levels in organs with high energy requirements, such as the liver and the heart.

B. Compositions

In a preferred embodiment, the route of administration is topical. In a related embodiment, the composition is a preparation selected from the group consisting of an ointment, cream, emulsion, lotion and gel for topical administration. In one aspect of this embodiment, the pharmaceutical composition comprising CoQ10 is a topical cream.

Compositions comprising Coenzyme Q10 can be applied to the blister and/or wound site, to an area of skin containing part or all of a blister and/or wound, to intact skin or to the entire skin surface, including the blister and/or wound site and intact skin, e.g., intact skin directly surrounding the blister and/or wound. In certain exemplary embodiments, the composition comprising CoQ10 is applied to a blister and/or wound on the skin. In other exemplary embodiments, the composition comprising CoQ10 is applied to intact skin. In certain embodiments, the CoQ10 composition are applied after each regular dressing change of the blister and/or wound.

It is preferable to present the active ingredient, i.e. CoQ10, as a pharmaceutical formulation. The active ingredient may comprise, for topical administration, from about 0.001% to about 20% w/w, by weight of the formulation in the final product, although it may comprise as much as 30% w/w, preferably from about 1% to about 20% w/w of the formulation. The topical formulations of the present invention comprise an active ingredient together with one or more acceptable carrier(s) therefor and optionally any other therapeutic ingredients(s). The carrier(s) should be "acceptable" in the sense of being compatible with the other ingredients of the formulation and not deleterious to the recipient thereof.

In treating a subject exhibiting a disorder of interest, e.g. a subject with Epidermolysis Bullosa, a therapeutically effective amount of an agent or agents such as these is administered. A therapeutically effective dose refers to that amount of the compound that results in amelioration of symptoms or a prolongation of survival in a subject.

Creams according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogels. The formulation may incorporate any suitable surface active agent such as an anionic, cationic or non-ionic surface active such as sorbitan esters or polyoxyethylene derivatives thereof. Suspending agents such as natural gums, cellulose derivatives or inorganic materials such as salicaceous silicas, and other ingredients such as lanolin, may also be included.

In certain embodiments of the invention, methods are provided for treating Epidermolysis Bullosa in a subject in need thereof by topically administering an effective amount of Coenzyme Q10 to the subject. In one aspect of this embodiment, the subject is administered a topical dose of Coenzyme Q10 to the target skin tissue, e.g. the skin blister, wound, or intact skin, in the range of about 0.01 to about 0.5 milligrams of coenzyme Q10 per square centimeter of skin. In one embodiment, Coenzyme Q10 is applied to the target tissue, e.g. the skin blister, wound or intact skin, in the range of about 0.09 to about 0.15 mg CoQ10 per square centimeter of skin. In various embodiments, Coenzyme Q10 is applied to the target tissue, e.g. the skin blister, wound or intact skin, in the range of about 0.001 to about 5.0, about 0.005 to about 1.0, about 0.005 to about 0.5, about 0.01 to about 0.5, about 0.025 to about 0.5, about 0.05 to about 0.4, about 0.05 to about 0.30, about 0.10 to about 0.25, or about 0.10 to 0.20 mg CoQ10 per square centimeter of skin. In other embodiments, Coenzyme Q10 is applied to the target tissue, e.g. the skin blister, wound or intact skin, at a dose of about 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, 0.25, 0.26, 0.27, 0.28, 0.29, 0.30, 0.31, 0.32, 0.33, 0.34, 0.35, 0.36, 0.37, 0.38, 0.39, 0.40, 0.41, 0.42, 0.43, 0.44, 0.45, 0.46, 0.47, 0.48, 0.49 or 0.5 mg CoQ10 per square centimeter of skin. In one embodiment, Coenzyme Q10 is applied to the target tissue at a dose of about 0.12 mg CoQ10 per square centimeter of skin. It should be understood that ranges having any one of these values as the upper or lower limits are also intended to be part of this invention, e.g., about 0.03 to about 0.12, about 0.05 to about 0.15, about 0.1 to about 0.20, or about 0.32 to about 0.49 mg CoQ10 per square centimeter of skin.

In another embodiment of the invention, the Coenzyme Q10 is administered in the form of a CoQ10 cream, wherein the CoQ10 cream comprises between about 0.1% and 25% of Coenzyme Q10. In other embodiments, the CoQ10 cream comprises about 0.1%, 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5%, 20%, 20.5%, 21%, 21.5%, 22%, 22.5%, 23%, 23.5%, 24%, 24.5%, or 25% of Coenzyme Q10. In another embodiment of the invention, the Coenzyme Q10 is administered in the form of a CoQ10 cream, wherein the CoQ10 cream comprises between about 1% and 5% of Coenzyme Q10. In one embodiment, the CoQ10 cream comprises about 3% of Coenzyme Q10. In other embodiments, the CoQ10 cream comprises about 1%, 1.5%, 2%, 2.5%, 3%, 3.5%, 4%, 4.5% or 5% of Coenzyme Q10. In various aspects of the above embodiments, the CoQ10 cream is administered at a dosage of about 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5 or 10 milligrams of CoQ10 cream per square centimeter of skin. It should be understood that ranges having any one of these values as the upper or lower limits are also intended to be part of this invention, e.g., between about 0.5 and about 5.0, about 1.5 and 2.5, or about 2.5 and 5.5 mg CoQ10 cream per square centimeter of skin.

Certain aspects of the invention provide a method for treating Epidermolysis Bullosa in a subject in need thereof, by topically administering Coenzyme Q10 to the subject such that treatment occurs, wherein the Coenzyme Q10 is topically applied one or more times per 24 hours for a treatment duration of six weeks or more. In certain aspects of the invention, the CoQ10 cream is applied twice every 24 hours for a treatment duration from about one to about twelve weeks. In certain aspects of the invention, the CoQ10 cream is applied once every 24 hours for a treatment duration from about one to about twelve weeks. In certain aspects of the invention, the CoQ10 cream is administered once every 48 hours for a treatment duration from about one to about twelve weeks. In certain aspects of the invention, the CoQ10 cream is administered twice a week for a treatment duration from about one to about twelve weeks. One embodiment of the present invention is a method of treating Epidermolysis Bullosa (EB) in a subject in need thereof, comprising topical administration of a pharmaceutical composition comprising a therapeutically effective amount of CoQ10 to the subject, wherein treatment of the subject results in the reduction of size of one or more blisters and/or wounds by at least about 70% after administration of an effective amount of CoQ10 for a treatment duration of about four weeks. One embodiment of the present invention is a method of treating Epidermolysis Bullosa (EB) in a subject in need thereof, comprising topical administration of a pharmaceutical composition comprising a therapeutically effective amount of CoQ10 to the subject, wherein treatment of the subject results in the reduction of size of one or more blisters and/or wounds by at least about 20% to 80% after administration of an effective amount of CoQ10 for a treatment duration of about four to about eight weeks. In one aspect of the above embodiment, the reduction in blister and/or wound size is about 20%, 21%, 22%, 23%, 24%, 25%, 26%, 27%, 28%, 29%, 30%, 31%, 31%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, or 80% for any of the treatment durations described immediately below.

In any of the forgoing aspects of the invention, the duration of treatment may typically be from two to twelve weeks, or until the blister and/or wound heals. In one aspect of the invention, the treatment duration is about one week. In another aspect of the invention, the treatment duration is about two weeks. In another aspect of the invention, the treatment duration is about three weeks. In another aspect of the invention, the treatment duration is about four weeks. In another aspect of the invention, the treatment duration is about five weeks. In another aspect of the invention, the treatment duration is about six weeks. In another aspect of the invention, the treatment duration is about seven weeks. In another aspect of the invention, the treatment duration is about eight weeks. In another aspect of the invention, the treatment duration is about nine weeks. In another aspect of the invention, the treatment duration is about ten weeks. In another aspect of the invention, the treatment duration is about eleven weeks. In another aspect of the invention, the treatment duration is about twelve weeks. In another aspect of the invention, the treatment duration is until the target lesion is sufficiently healed. In another aspect of the invention, the treatment duration is chronic (with no discreet end point), as a subject suffering from EB has habitual blisters and/or wounds which require treatment with a pharmaceutical composition comprising CoQ10 of the present invention.

In preferred embodiments of the invention, the composition comprising CoQ10 is applied to a blister on the skin. In other embodiments of the invention, the composition comprising CoQ10 is applied to intact skin. In one aspect of the invention, the pharmaceutical composition is the CoQ10 3% cream which is described in International Publication No. WO2008/116135, the entire content of which is incorporated by reference in its entirety herein.

C. Combination Therapies

In certain embodiments, CoQ10 and/or pharmaceutical compositions thereof can be used in combination therapy with at least one other therapeutic agent. CoQ10 and/or pharmaceutical composition thereof and the other therapeutic agent can act additively or, more preferably, synergistically. In one embodiment, CoQ10 and/or a pharmaceutical composition thereof is administered concurrently with the administration of another therapeutic agent. In another embodiment, a compound and/or pharmaceutical composition thereof is administered prior or subsequent to administration of another therapeutic agent.

In one embodiment, an additional agent for use in the therapeutic methods of the invention are agents that can control pain and itching and address complications such as infection in Epidermolysis Bullosa. Certain exemplary additional agents include vasodilators, vasoconstrictors, hypertensive agents, antibacterial agents, antibiotics, antioxidants, antifungal agents, non-steroidal anti-inflammatory agents, steroidal agents, and anesthetics.

In another embodiment, an additional agent for use in the combination therapies of the invention is a biologic agent. Biological agents are the products of a biological system, e.g., an organism, cell, or recombinant system. Examples of such biologic agents include nucleic acid molecules (e.g., antisense nucleic acid molecules), interferons, interleukins, colony-stimulating factors, antibodies, e.g., monoclonal antibodies, anti-angiogenesis agents, and cytokines. Exemplary biologic agents are discussed in more detail below and generally belong to various classes including, for example: Hormones, hormonal analogues, and hormonal complexes, e.g., estrogens and estrogen analogs, progesterone, progesterone analogs and progestins, androgens, adrenocorticosteroids, antiestrogens, antiandrogens, antitestosterones, adrenal steroid inhibitors, and anti-leuteinizing hormones; and enzymes, proteins, peptides, polyclonal and/or monoclonal antibodies, such as interleukins, interferons, colony stimulating factor, etc.

It should be noted that more than one additional agent, e.g., 1, 2, 3, 4, 5, may be administered in combination with CoQ10. For example, in one embodiment two additional agents may be administered in combination with CoQ10. In another embodiment, a chemotherapeutic agent, a biologic agent, and CoQ10 may be administered.

Various forms of the biologic agents may be used. These include, without limitation, such forms as proform molecules, uncharged molecules, molecular complexes, salts, ethers, esters, amides, and the like, which are biologically activated when administered to the target site.

3. Methods of Treatment

The present invention is based upon the surprising finding that one or more structural and/or functional proteins, such as, but not limited to a keratin, a collagen, a plectin, an annexin, a vimentin, a filamin, an integrin and a laminin, is defective in the skin of subjects with EB. Therefore, in certain embodiments, the present invention aims to treat a blister and/or wound in a subject with EB by increasing the expression and/or activity of the one or more structural or functional proteins that is defective in the skin of the EB subject.

A. Epidermolysis Bullosa

Epidermolysis bullosa (EB) is a chronic genetic blistering skin disorder characterized by blister and/or wound formation when minor mechanical trauma, friction, or heat is applied to the skin. The skin of a subject with EB is characterized by extreme skin fragility compared to the skin of a subject without EB. The skin of people who have EB is so fragile that minor rubbing, or even environmental conditions such as heat and humidity can cause blistering and/or wounds. There is a wide spectrum of severity in EB: the mildest form is localized EB simplex, where the symptoms include blistering predominantly on the feet and hands, but other forms, notably recessive dystrophic EB (RDEB) and junctional EB, are characterized by more extensive skin and mucosal involvement, systemic complications, disfigurement, and often severely limited life expectancy. It is persons with these more severe forms of EB who have a tendency to develop lifelong chronic wounds and infections (Pope et al., 2013).

Pearson in 1962 proposed a sophisticated classification system for EB based on the findings of transmission electron microscopy (TEM) (Pearson R W., 1962). Depending on the ultrastructural levels within which the split develops in EB skin, either spontaneously or following minor trauma, he classified EB into three major types: epidermolytic (EB simplex; EBS), lucidolytic (junctional EB; JEB) and dermolytic (dystrophic EB; DEB).

Advanced diagnostic techniques such as immunofluorescence antigen mapping (IFM) or transmission electron microscopy (TEM) can also be employed to diagnose and classify EB. The primary advantage of TEM is that it can visualize ultra-structural abnormalities and provide a semi-quantitative assessment of specific epidermal keratinocyte-basement membrane zone (BMZ) structural deficits. (McMillan, 1998). TEM may be particularly useful in patients with mild DEB or EBS; IFM may be normal in these cases, but TEM shows morphological abnormalities of anchoring fibrils or intermediate filaments. Sometimes a split may not be visible in an IFM sample, but TEM can show an ultrastructural split. Multiple cleavage planes as seen in Kindler syndrome may be appreciated only by TEM. The diagnostic precision of IFM is similar to that of TEM with the advantage that it is simpler and faster both to perform and to interpret. Further, with the use of specific monoclonal antibodies, IFM can provide considerable insight into not only the major subtypes of EB but also into the most likely mutated structural protein (Fine et al., 2008). A recent study has also shown the utility of IFM in the prenatal diagnosis of certain types of severe EB by studying first trimester chorionic villous biopsy (D'Alessio et al., 2008).

Epidermolysis Bullosa Simplex (EBS): The most common type of EB simplex is localized EB simplex with skin cleavage within the basal layer of the epidermis. The blisters are usually on the palms and soles, aggravated by heat and friction. The inheritance is autosomal dominant with mild disease. Mutations are present in keratins 5 or 14. A less common but also autosomal dominant type, Dowling-Meara, features clustered distal blisters with a string of pearl-like arrangement. Although painful keratoderma is noted with time, patients' symptoms tend to be less severe with increasing age. In cases of EBS, all antibodies are found at the base of the blister. Additional EBS-specific antibodies (e.g., for keratin 5 and 14, plectin and α6β4 integrin) may be employed; in general, expression of proteins is normal, except in autosomal recessive EBS, when patients may have absent keratin 14 staining (Yiasemides E et al., 2008).

Junctional EB (JEB): Skin and mucosal cleavage occurs at the lamina lucida level of the basement membrane zone, including periorificial areas of skin, ocular, tracheolaryngeal, gastrointestinal, genitourinary, and renal systems. The mode of inheritance is usually autosomal recessive, with mutations in the genes encoding collagen XVII, α6β4 integrin, or laminin 332. The Herlitz form is the most severe (exuberant granulation in the perioral area, around the nails, and denuded diaper area), with death in most cases in the first 1 to 2 years of life. The non-Herlitz form is often severe in infancy, but life expectancy is considerably longer. The main target proteins in JEB are type XVII collagen (BP180 or BPAG2) and laminin 332 (previously laminin 5). Collagen XVII is expressed on the roof of split skin whereas other antibodies are seen on the floor of the blister. In the severe Herlitz form of JEB (JEB-H), caused by mutations in one of the genes encoding the three polypeptide chains of laminin 332, expression of this protein is absent or markedly reduced. In cases of non-Herlitz JEB (JEB-nH) there is reduced staining of laminin 332. In cases where there is a collagen XVII mutation, there is marked reduction or absence of expression of collagen at the BMZ with normal expression of laminin 332. In JEB with pyloric atresia, staining to a6 and (34 integrin subunits is reduced or absent (Pohla-Gubo G. et al., 2010). Type IV collagen staining in all forms of JEB localizes to the blister floor.

Dystrophic EB (DEB): This type of EB involves cleavage beneath the lamina densa, within the dermis at the level of the anchoring fibrils due to mutations in the type VII collagen gene. All DEB subtypes are caused by mutations in type VII collagen which is the principal component of anchoring fibrils. The level of cleavage occurs in the sublamina densa with collagen XVII and laminin 332 staining seen in the roof of the blister. In patients with severe generalized recessive DEB (RDEB), IFM shows absent or barely detectable type VII collagen. In these cases, immunostaining of type IV collagen occurs on the roof and indicates dermolytic blistering to confirm DEB. Other generalized or localized subtypes of DEB may show a reduced or normal expression of type VII collagen (Pohla-Gubo G. et al., 2010; Cepeda-Valdes R, et al., 2010). The autosomal dominant form is the second most common EB type, and patients present with blisters in areas prone to bumps or knocks such as the toes, knees, fingers, and elbows. The autosomal recessive form is usually more debilitating, with blisters from birth and pseudosyndactyly, where toes and fingers become fused. This form is associated with lifelong chronic wounds and with the development of aggressive squamous cell carcinomas in the 30s to 40s. If they reach their mid-50s, 90% of individuals will have had a squamous cell carcinoma.

Kindler Syndrome: This rare form of EB may result in cleavage at any of the 3 levels outlined above. Blisters in early childhood are gradually replaced by scarring, keratoderma (thickened palms and soles), poikiloderma (hypopigmentation and hyperpigmentation, telangiectasia, and atrophy), and photosensitivity. It is caused by mutations in the gene encoding kindlin 1, which is involved in basal layer keratinocyte adhesion at focal contacts. IFM using a standard panel of BMZ antibodies does not show any reduction or major alteration in staining intensity though type IV and VII collagen antibodies may show broad, reticular staining at the dermal-epidermal junction. Labeling of normal skin with a novel, polyclonal antibody against kindlin-1 shows a bright staining in the epidermis, particularly in the basal keratinocytes and along the dermal-epidermal junction without any dermal alterations. In contrast, in Kindler syndrome skin there is a marked reduction and, in some cases, a complete absence of staining in the epidermis (Ashton G H. 2004).

Figure 6:
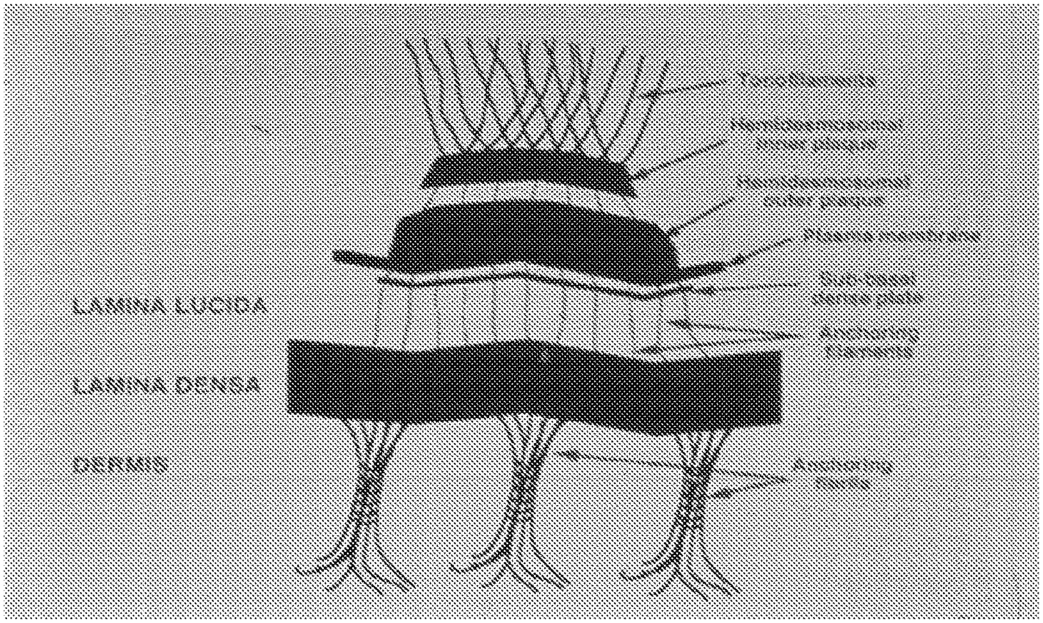
FIG. 6 is a schematic that shows the structure of the cutaneous basement membrane zone (BMZ).
Figure 7:
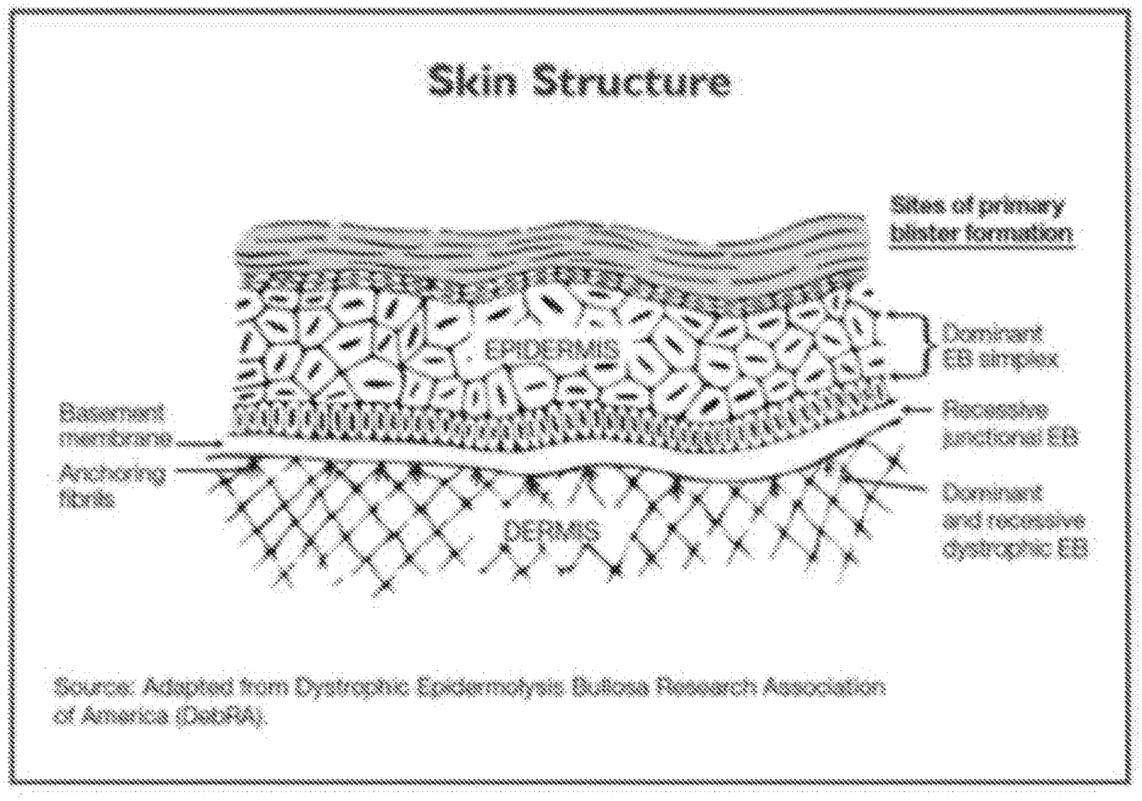
FIG. 7 is a schematic that shows skin layers affected in patients with EB.

The structure of the cutaneous basement membrane zone is shown in FIG. 6.

B. EB Wound Healing

The inflammatory phase is the first phase of normal wound healing and occurs immediately following trauma. The first step of wound healing involves the formation of a blood clot. This is then followed by inflammation, which is characterized by localized erythema, edema, and tenderness. Once this inflammation of the wound resolves, the proliferative phase of wound healing begins. This is where cellular proliferation, fibroblast proliferation, and epidermal cell division occurs. During this phase, new blood vessels are formed and granulation tissue gradually fills the wound. Once the wound is filled with granulation tissue, epidermal cell migration occurs along the border of the wound in order to close it. The last phase of wound healing, the remodeling phase, begins once the epidermal cell migration is complete. During this phase, scar tissue has formed and matures, strengthens, and gradually thins, softens, and blends with uninjured skin (Schober-Flores, 2003).

It is generally well accepted that the wound healing process in EB patients is severely compromised, remaining in the inflammatory phase for prolonged time without progression into the healing phases (Schober-Flores, 1999). The healing process is further impaired due to multiple factors including infection, nutritional status, tissue oxygenation status and medications typically used for symptomatic treatment of the disease such as corticosteroids (Marinkovich et al, 2014).

As discussed above, patients with EB have a defect in the expression and/or activity of one or more structural and/or functional proteins, such as, but not limited to a keratin, a collagen, a plectin, an annexin, a vimentin, a filamin, an integrin and a laminin, which changes essential characteristics of the skin and prevents it from healing in a normal way.

Accordingly, in one aspect, the present invention features a method of improving the structural integrity of the skin of a subject suffering from EB, comprising topical administration of a composition comprising a therapeutically effective amount of CoQ10 to the skin, thereby improving the structural integrity of the skin. In one embodiment, the skin comprises a deficiency in a structural and/or functional protein. In one embodiment, the deficiency in the structural and/or functional protein is within the epidermis. In another embodiment, the deficiency in the structural and/or functional protein is within lamina lucida. In another embodiment, the deficiency in the structural and/or functional protein is in the sublamina densa zone. In one embodiment, the EB is Epidermolysis Bullosa Simplex. In another embodiment, the EB is Junctional Epidermolysis Bullosa. In another further embodiment, the EB is Dystrophic Epidermolysis Bullosa. In another embodiment, the deficiency in a structural and/or functional protein is a deficiency in protein activity or protein expression. In another embodiment, the deficiency in activity or expression is determined by histological examination, immunofluorescence imaging or Real Time Quantitative PCR. In another embodiment, structural integrity is determined by histological examination, transmission electron microscopy (TEM) or immunofluorescent staining of a skin biopsy from the subject.

In certain embodiments, an improvement in the structural integrity is determined by quantifying the number of new blisters and/or wounds formed on the skin of a subject suffering from EB that is treated with CoQ10, compared to the skin of a subject suffering from EB that is not treated with CoQ10. Quantifying may be determined using image analysis of photographs of the blisters and/or wound.

In another embodiment, the structural integrity is measured using a suction blister test on the skin of a subject suffering from EB that is treated with CoQ10, compared to the skin of a subject suffering from EB that is not treated with CoQ10. In another embodiment, the time to blister formation in skin treated with CoQ10 is greater than the time to blister formation in skin not treated with CoQ10.

In another aspect, the present invention features a method of treating a wound of the skin in a subject, wherein the skin comprises a deficiency in one or more structural and/or functional proteins, comprising topical administration of a composition comprising a therapeutically effective amount of CoQ10 to the wound, thereby treating the wound in the subject. In another embodiment, the subject suffers from Epidermolysis Bullosa (EB), for example Epidermolysis Bullosa is Epidermolysis Bullosa Simplex, Junctional Epidermolysis Bullosa, Dystrophic Epidermolysis Bullosa or Kindler's Syndrome. In one embodiment, the structural or functional protein is selected from the group consisting of: a keratin, a collagen, a plectin, an annexin, a vimentin, a filamin, an integrin and a laminin. For example, the keratin protein may be selected from the group consisting of: keratin 5 (KRT5), keratin 13 (KRT13), keratin 14 (KRT14) and keratin 17 (KRT17). In another embodiment, the collagen protein is selected from collagen XVII or type VII collagen. In another embodiment, the laminin is laminin 332. In another embodiment, the integrin is $\alpha6\beta4$ integrin. In one aspect, topical administration of a pharmaceutical composition comprising CoQ10 leads to an increase in collagens, plectin, laminin, vimentin, annexin, KRT13, KRT14 and/or KRT17, as well as an increase in fibroblasts and/or keratinocytes.

In certain embodiments, treating the wound is determined by the percentage of wound closure of the wound of a subject treated with CoQ10 compared to the initial wound area and the wound of a subject not treated with CoQ10 compared with the initial wound area. For example, the percentage of wound closure can be determined using image analysis of photographs of the wound. In one embodiment, the percentage of wound closure is greater than 50%. In another embodiment, the percentage of wound closure is greater than 75%. In another embodiment, the percentage of wound closure is greater than 85%. In another embodiment, the percentage of wound closure is greater than 90%. In another embodiment, the percentage of wound closure is greater than 95%. In one embodiment, the percentage of wound closure is between 50-99%, for example 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 or 99%.

In another aspect, the invention features a method of increasing the rate of healing of a skin blister and/or wound in a subject suffering from EB, comprising topical administration of a composition comprising a therapeutically effective amount of Coenzyme Q10 (CoQ10) to the skin blister, thereby increasing the rate of healing of the skin blister and/or wound in the subject. In one embodiment, the deficiency in the structural and/or functional protein is within the epidermis. In another embodiment, the deficiency in the structural and/or functional protein is within lamina lucida. In another embodiment, the deficiency in the structural and/or functional protein is in the sublamina densa zone. In one embodiment, the EB is Epidermolysis Bullosa Simplex. In another embodiment, the EB is Junctional Epidermolysis Bullosa. In another further embodiment, the EB is Dystrophic Epidermolysis Bullosa. In another embodiment, the EB is Kinder's Syndrome. In another embodiment, the deficiency in a structural and/or functional protein is a deficiency in protein activity or protein expression. In another embodiment, the deficiency in activity or expression is determined by histological examination, immunofluorescence imaging or Real Time Quantitative PCR.

In one embodiment, the rate of healing is determined by the percentage of wound closure of the wound of a subject treated with CoQ10 compared to the initial wound area and the wound of a subject not treated with CoQ10 compared with the initial wound area. In one embodiment, the percentage of wound closure is greater than 50%. In another embodiment, the percentage of wound closure is greater than 75%. In another embodiment, the percentage of wound closure is greater than 85%. In another embodiment, the percentage of wound closure is greater than 90%. In another embodiment, the percentage of wound closure is greater than 95%. In one embodiment, the percentage of wound closure is between 50-99%, for example 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 or 99%. In another embodiment, the rate of healing is determined by the rate of re-epithelialization of the skin blister and/or wound treated with the CoQ10 composition is increased compared to the rate of re-epithelialization of an untreated blister and/or wound. In another further embodiment, the rate of healing is determined by a reduction in an epidermal gap distance of the skin blister and/or wound treated with the CoQ10 composition compared to the epidermal gap distance of an untreated skin blister and/or wound.

In one aspect, the present invention features methods of treating skin blistering and/or wounds in a subject in need thereof, comprising topical administration of a composition comprising a therapeutically effective amount of Coenzyme Q10 (CoQ10) to the skin of the subject, thereby treating skin blistering and/or wounds in the subject. In one embodiment, the subject suffers from Epidermolysis Bullosa (EB).

In one embodiment of the present invention, administration of the composition comprising a therapeutically effective amount of CoQ10 decreases the time to healing of the blister and/or wound compared to an untreated blister and/or wound.

In another embodiment, administration of the composition comprising a therapeutically effective amount of CoQ10 improves the quality of healing using the Epidermolysis Bullosa Disease Activity and Scarring Index (EBDASI) compared to an untreated blister and/or wound.

The present invention also features, in other aspects, methods of promoting healing of a skin blister and/or wound in a subject suffering from Epidermolysis Bullosa, comprising topical administration to the blister of a composition comprising a therapeutically effective amount of Coenzyme Q10 (CoQ10), thereby promoting healing of the skin blister and/or wound in the subject.

In one embodiment, the rate of re-epithelialization of the blister treated with the CoQ10 composition is increased compared to the rate of re-epithelialization of an untreated blister. Methods for assessing the rate of re-epithelialization are described herein below.

In one embodiment, the quality of epidermal integrity of the blister and/or wound treated with the CoQ10 composition is improved compared to the quality of epidermal integrity of an untreated blister and/or wound. Methods for assessing the quality of epidermal integrity described hereinbelow. In one embodiment, the quality of epidermal integrity is assessed using histologic examinations of the blister roof.

This skin of a subject with EB is missing anchors or proteins that hold normal skin together. As a result, trivial pressure on the skin causes blistering. The ability of CoQ10 to influence expression of structural proteins that are involved in maintenance of skin structure and function, along with its ability to influence critical phases of the wound healing process provides compelling rationale for its utility in potential treatment of wounds in EB. Thus, the present invention is based, in part, on the identification that the expression of certain structural proteins is increased or decreased in the skin of subjects with EB, and that treatment with the CoQ10 compositions of the invention can alter the expression of particular structural proteins.

In certain embodiments, the level of expression of one or more structural proteins in the blister and/or wound treated with the CoQ10 composition is modulated in comparison to the level of expression of the one or more structural proteins in an untreated blister and/or wound. As a result, a particular patient population that has an alteration in the expression of one or more particular structural proteins can be chosen for treatment with the CoQ10 compositions of the invention. Accordingly, the invention also features methods of treating a subject with Epidermolysis Bullosa, comprising administration to the subject of a composition comprising a therapeutically effective amount of CoQ10, thereby treating the subject. In one embodiment, the subject is identified as having an alteration in the expression of one or more structural proteins in the skin.

In certain embodiments, structural proteins include collagens, plectin, annexins, vimentin, filamins and laminins. In particular embodiments, the structural protein is a keratin, and in particular keratin 5 (KRT5), keratin 13 (KRT13), keratin 14 (KRT14) and keratin 17 (KRT17).

In another aspect, the invention features a method of treating or preventing squamous cell carcinoma in a subject suffering from Epidermolysis Bullosa, comprising topical administration of a composition comprising a therapeutically effective amount of CoQ10 to the subject, thereby treating or preventing squamous cell carcinoma in the subject. In one embodiment, the composition comprising CoQ10 is administered to squamous cell carcinoma cells in the subject. In another embodiment, the squamous cell carcinoma is cutaneous squamous cell carcinoma. In one embodiment, administration of the composition comprising CoQ10 modulates the expression of one or more proteins in the subject. In a further embodiment, the protein is a stress protein or structural protein. In another further embodiment, the protein is selected from the group consisting of transaldolase 1, NM23 protein, heat shock 27 kDa protein 1, keratin 1, keratin 14, keratin 13, proteasome beta 7, proteasome activator subunit 3, and rho GDP dissociation inhibitor alpha. In another embodiment, the protein is selected from the group consisting of: V-akt murine thymoma viral oncogene homolog 1 (AKT1), BCL2-associated athanogene 4 (BAG4), BCL2-associated X protein (BAX), BCL2-like 1 (BCL2L1), BCL2/adenovirus E1B 19 kDa interacting protein 3 (BNIP3), caspase recruitment domain family, member 6 (CARD6), caspase 6, apoptosis-related cysteine peptidase (CASP6), caspase 7, apoptosis-related cysteine peptidase (CASP7), growth arrest and DNA-damage-inducible, alpha (GADD45A), tumor protein p53 (TP53) and tumor protein p73 (TP73).

4. Methods of Assessing the Therapeutic Effect of CoQ10 Compositions

The therapeutic effect of the CoQ10 compositions in treating skin blistering and/or wound in a subject in need thereof, e.g. a subject suffering from EB, can be evaluated in a number of different ways in the subject, including a reduction in pain, improvement in quality of life, time to healing, quality of healing, increased resistance to trauma, and reduction in blister and/or wound formation.

In certain embodiments, the quality of healing can be assessed using the Epidermolysis Bullosa Disease Activity and Scarring Index (EBDASI). EBDASI, quantifies the overall severity of involvement of the skin, scalp, mucous membranes, nails, and other epithelialized surfaces in terms of activity and damage. The advantage of the EBDASI is the ability to distinguish activity scores that are responsive to therapy separately from damage, thus enabling physicians to follow disease activity that is potentially reversible that prevents damage. The EBDASI is a 4-page document (see FIG. 1 and Supplemental Figure 1 of Loh et al, 2014, incorporated by reference in its entirety herein). In the EBDASI, each area of the skin was examined in order from top to bottom at 12 different anatomical sites. Activity (blistering/erosions/crusting) is scored out of 10 in each area. The features of damage (erythema, dyspigmentation, poikiloderma, skin atrophy, hyperkeratosis/scaling, scarring, milia) are given a 0 for absent and 1 for present in each site. The process is continued for the scalp, mucous membranes, nails, and other epithelialized surfaces.

Another framework that can be used for wound assessment is the modified MEASURE paradigm (measure size, exudate [amount and characteristics], appearance [base or granulation tissue], suffering [pain], undermining [depth measured in centimeters], re-evaluate, and edge) (Keast et al., 2004, incorporated by reference in its entirety herein). This documentation provides a good assessment of the extent of the wound in its current state, as well as a good tool for monitoring the healing process. A modified model tailored to patients with EB is outlined in Pope et al., 2013.

In certain embodiments, the formation of granulation tissue in EB subjects is quantified by serial photography.

Time to healing can be assessed as a blister and/or wound being "healed" (completely closed without drainage) or "not healed." In certain embodiments, the time to healing can be defined as the first date that healing is observed minus the date that the blister and/or wound is first identified. For example, if a blister and/or wound is first identified at day 1, and the blister and/or wound is identified as "healed" on day 10, then the time to healing is 9 days. In one embodiment, the time course of wound healing is documented with photograph, dermoscopic photo and Reflectance Confocal Microscopy (RCM) evaluation.

Reflectance Confocal Microscopy

Reflectance confocal microscopy (RCM) offers in vivo, non-invasive imaging technology with resolution at the cellular level, which correlates well with histopathology. RCM provides rapid assessment of the lesion and in vivo, enables the visualization of epidermis and upper dermis in real time. Accordingly, healing of the skin blister and/or wound can be assessed using reflectance confocal microscopy (RCM).

During the 1990s, the RCM was developed to image the skin in real-time and for use that was suitable for clinical applications. (Rajadhyaksha M, et al, 1999) A commercially available RCM (VIVASCOPE 1500, Lucid Inc, Rochester, N.Y., USA) uses a near-infrared 830 nm diode laser and low-power laser beam up to 22 mW for imaging. The light beam scans the skin to obtain a horizontal optical section, and presents gray scale images (500×500 μm field-of-view) as well as mosaic images of the skin ("Vivablock"). In addition, it can produce a series of single images stacked vertically ("Vivastack") at the same point in the tissue. RCM maximum in-vivo imaging depth is approximately 250-350 μm. (Reflectance confocal microscopy of cutaneous tumors: an atlas with clinical, dermoscopic and histological correlations: Informa Healthcare; 2008.)

Normal skin layers (stratum corneum, spinous and granular, suprabasal, dermal-epidermal junction and superficial dermis), have been characterized using RCM. These results were reproducible. In addition, other skin structures and cells have been identified, including blood vessels, hair follicles, sweat glands, keratinocytes, inflammatory cells and melanocytic cells. Currently, RCM is used in basic skin research, cosmetic research, and clinical dermatology. Its primary use has been the early detection of melanoma and non-melanoma skin. (Yamashita, et al, 2005; Langley et al, 2001)

Traditionally, routine wound assessment is based on the clinical evaluation of wound characteristics. While visual inspection is the established procedure in clinical dermatology, the method is inherently subjective, often yielding inaccurate descriptions of wound conditions, and does not permit an ultrastructural analysis of the wound tissue. (Lange-Asschenfeldt, et al, 2012) Hence, routine histology remains the gold standard for morphologic evaluation of cutaneous wound healing. However, while histology still plays an important role in skin research, there are substantial limitations. The invasive character of biopsies does not allow an assessment over time of the same area of tissue where the biopsy was taken, and biopsies may not be feasible for evaluation of large or recurrent wounds or patients with significant impairment of wound healing or high risk of infection. In addition, tissue removal and histological processing may result in artifacts, further limiting its clinical applicability.

Considering these limitations, a number of noninvasive imaging techniques have been evaluated for their applicability to assess human skin wounds at different stages of wound healing. These techniques can be used in the present invention to assess the healing of skin blisters and/or wounds in subject with EB. Among them, in vivo RCM represents an innovative optical imaging tool for noninvasive evaluation of the skin in real time. Altintas and coworkers first employed RCM for evaluation of burn wounds, whereby aspects of microcirculation, inflammation, and histomorphology were described. Confocal microscopy has also been used to evaluate acute epidermal wound healing after fractional laser therapy (Sattler, et al, 2013) and in a human model of tissue damage induced by cryosurgery. (Terhorst, et al, 2011)

The completely noninvasive nature and high-resolution capability of a confocal microscope makes it a useful instrument in wound healing research and—given its cellular resolution of epidermal and superficial dermal structures—particularly useful in wound healing in epidermal injury models. The characterization of the process of wound healing resulting from this research may improve our knowledge in this topic, give a valuable tool to evaluate wound healing in clinical practice, and provide a non-invasive technique to test the influence of topical products in the process of wound healing.

In certain embodiments, the time course of wound healing is documented with photographs, dermoscopic photo and RCM evaluation. RCM evaluation parameters will include features of cutaneous wound repair on a cellular, morphological and architectural level, as well as the documentation of dynamic processes such as blood flow and inflammation, and the successive events of wound healing.

In other embodiments, quality of life can be measured using the Lansky Performance Scale and the Children's Dermatology Life Quality Index, as described herein and in Lewis-Jones et al., 1995, incorporated by reference in its entirety herein.

In one embodiment, the rate of re-epithelialization of the blister and/or wound treated with the CoQ10 composition is increased compared to the rate of re-epithelialization of an untreated blister and/or wound. The rate of re-epithelialization can be examined and compared using reflectance confocal microscopy (RCM) evaluation.

In one embodiment, an epidermal gap distance of the blister and/or wound is reduced in comparison to an epidermal gap distance of an untreated blister and/or wound. Changes in the epidermal gap distance can be determined by the gap width can be quantified as the distance of the gap between the two migrating multilayered epithelial fronts across the blister and expressed as % open blister/wound=[blister/wound width (mm)*100/initial blister/wound size]. Further, hematoxylin and eosin (HE) staining can be used to examine the tissue morphology.

In one embodiment, the quality of epidermal integrity of the blister and/or wound treated with the CoQ10 composition is improved compared to the quality of epidermal integrity of an untreated blister and/or wound. The quality of epidermal integrity can be determined by RCM evaluation.

It will be readily apparent to those skilled in the art that other suitable modifications and adaptations of the methods of the invention described herein are obvious and may be made using suitable equivalents without departing from the scope of the invention or the embodiments disclosed herein. Having now described the invention in detail, the same will be more clearly understood by reference to the following examples, which are included for purposes of illustration only and are not intended to be limiting

EXAMPLES

Example 1. Effect of Topical Coenzyme Q10 Cream in Patients with Epidermolysis Bullosa A Phase 1 study was undertaken to evaluate the safety, pharmacokinetics and therapeutic effect of topical Coenzyme Q10 (CoQ10) cream in patients with Epidermolysis Bullosa.

Trial Objectives

The primary objectives of the trial are to evaluate the safety and tolerability in patients with EB when treated with topical CoQ10 3.0% Cream applied as instructed from every other day to twice per week to wounded skin, and every day to a section of intact skin, as instructed. Safety observations and measurements that are assessed include study drug exposure, abnormal local skin reaction, adverse events, laboratory data (hematology, coagulation, and serum chemistry), vital signs, and concomitant medications.

The secondary objectives of the trial are to evaluate the pharmacokinetics (PK) of CoQ10 3.0% Cream in this patient population and to evaluate the therapeutic effect of topical CoQ10 3.0% Cream in this patient population as measured by a reduction in pain, improvement in quality of life, time to healing, quality of healing, increased resistance to trauma, and reduction in blister formation. The Epidermolysis Bullosa Disease Activity and Scarring Index (EB-DASI) and the Vancouver Scar Scale are utilized to quantify wound healing and scarring. EBDASI and the Vancouver Scar Scale are known in the art and are described in, for example, Journal of the American Academy of Dermatology 2014; 70:89-97, incorporated by reference in its entirety herein.

Investigational Product

Coenzyme Q10 3.0% is a deep yellow-orange powder and is very hydrophobic with a melting point of approximately 48 degrees centigrade. The active ingredient, CoQ10 3.0% Cream, ubidecarenone, USP may be adversely affected by heat and light, according to the literature. Experimentation with various concentrations (25-60%) of CoQ10 solubilized in Polysorbate 80, showed no measurable breakdown of CoQ10 in this mixture when heated for several hours at 55° C. Heating the mixture to 50-55° C. (i.e., 2-7° C. above the melting point of CoQ10) greatly speeds the solubilization of CoQ10. To manufacture the topical CoQ10 cream, two CoQ10 concentrate phases (CoQ10/Polysorbate 80 and water-lecithin-glycol-phenoxyethanol) were each heated separately to 50-55° C. with the water phase added to the solubilized CoQ10 and were mixed with high shear homogenization to form a microemulsion concentrate of CoQ10. The CoQ10 concentrate was then added to a water-in-oil (W/O) cream emulsion base to produce the final CoQ10 cream. The final concentration of CoQ10 in the cream was 3.0%. The CoQ10 3% cream is further described in International Publication No. WO2008/116135, the entire content of which is incorporated by reference in its entirety herein.

Trial Population

Ten patients were enrolled in this study who have diagnosed epidermolysis bullosa of any subtype. Patients must meet the following criteria in order to be included in the clinical trial: 1. Male or female at least 12 years old at the time of screening; 2. Have confirmed EB diagnosis; 3. Have no other dermatological disease that may adversely impact wound healing; 4. Are willing to refrain from using non-approved lotions or creams during the treatment period and from washing the treated area until the next application is done; 5. Are willing to refrain from exposure to excessive direct sunlight or ultraviolet light for the duration of the study; 6. Have laboratory values for the tests listed in the Study Schedule that are within the reference ranges as defined by the central laboratory, or have "out of range" test results that are clinically acceptable to the investigator. Acceptable "out of range" values are generally those within the patient's normal baseline levels due to concurrent medications or disease processes with the exception of INR and PT/APTT; 7. Have a caregiver able to follow study instructions and likely to complete all study requirements; 8. Have a provided written informed consent by patient or a legal guardian, including consent for tissue to be examined and stored by the Department of Dermatology and Cutaneous surgery. If the patient is between 12 and 17 years of age, assent must be given by the patient; 9. Guardian has provided written consent to allow photographs of the target EB lesion(s) to be used as part of the study data and documentation; 10. Females of childbearing potential must have a negative pregnancy test at screening and be using an acceptable form of birth control (oral/implant/injectable/transdermal contraceptives, intrauterine device, condom, diaphragm, abstinence, or a monogamous relationship with a partner who has had a vasectomy); 11. Have an INR value of 0.8-1.2 as well as normal prothrombin time (PT)/activated partial thromboplastin time (APTT); 12. Have at least 1 active EB wound between 2.5 and 50 $cm^2$ in size.

Trial Design

Patients/caregivers applied 3% CoQ10 cream as instructed from every other day to twice per week to wounded skin, including a wound selected by the investigators to be the index wound, and every day to a section of intact skin as instructed. The index wound was followed for wound healing through clinical evaluation and photographs. The index wound was preferably located on the limb or on the trunk (but not intertriginous areas, or on the diaper area, if the patient is in diapers). A section of intact skin was selected for suction blisters evaluation and daily 3% CoQ10 cream application. The section of intact skin is on either the anterior thigh, or the mid to lower back, if the patient weighs less than 15 kg. The total area of trial medication (CoQ10 3.0% Cream) application was not to exceed 20% BSA. Safety Review Group (SRG) monitors safety on an ongoing basis. If adverse events (AEs), and all other safety parameters are acceptable, the study continues as planned. If the SRG determines a significant safety concern exists, no further treatment is given to any patient until a full evaluation has taken place. If the SRG determines there is a risk to continuing treatment, the study is stopped.

Safety and tolerability assessments consist of ongoing monitoring and recording of all AE and serious adverse event (SAE) reports, the regular monitoring of signs and symptoms of cutaneous irritation, and regular measurements of vital signs, physical examinations, and clinical laboratory tests (chemistry and hematology), including hemoglobin, hematocrit, white blood cell (WBC) count with differential (monocytes, eosinophils, basophils, neutrophils, lymphocytes) as percentage and absolute value, red blood cell (RBC) count, platelet count, and PT/APTT/INR Albumin, alkaline phosphatase, total bilirubin, bicarbonate/CO2, calcium, cholesterol, chloride, creatinine, creatine kinase, γ-GT, glucose, LDH, inorganic phosphorus, lipase, amylase, magnesium, potassium, total protein, AST, ALT, sodium, triglycerides, urea and uric acid. If the total bilirubin concentration is increased above 1.5 times the upper limit of normal, direct and indirect reacting bilirubin should be differentiated.

Administration of Trial Treatments

Trial Treatments: The initial application of study treatment (CoQ10 3.0% Cream) was made on Week 1, Day 1 in the clinic, monitored and guided by clinic staff, to confirm application to the index wound and other wounded skin, and to the unaffected skin selected. Thereafter, all study patients or their caregivers were required to apply the study treatment at home, including on trial center visit days. Trial medication was applied as instructed from every other day to twice per week to wounded skin, and every day to a section of intact skin as instructed.

Duration of Treatment: Each patient's overall participation was expected to be a maximum of 18 weeks. The duration of screening was up to 2 weeks. The duration of treatment period was 12 weeks. The duration of follow-up period was 4 weeks.

Prior and Concomitant Medications: No other creams or lotions were applied to the treatment area during the course of the study. All medications, including over the counter (OTC) drugs and nutritional supplements (including CoQ10 supplements), taken during the preceding 3 months were recorded at Screening. Thereafter, a record of all medications, including OTC drugs and nutritional supplements, taken during the course of the study was made. Information regarding the total daily dose, route of administration, start and discontinuation dates, and indication were recorded on the patient's case report form (CRF).

Overview

All patients visit the trial center on the days specified within this protocol. The complete Schedule of Assessments for this trial is shown below in Table 1.

TABLE 1

| Procedure | Wk 1 Day 1 | Wk 1 Day 3 | Wk 2 (+/−4 days) | Wk 3, 4, 5, 6, 7, 9, 10, 11 | Wk8 Day 1 (+/−2 days) | Wk 8 Day 3 (+/−2 days) | Wk 12 EOT (+/−2 days)[7] |
|---|---|---|---|---|---|---|---|
| Informed Consent/Assent | | | | | | | |
| Inclusion/Exclusion | x | | | | | | |
| Demographics/Med Hx/Wound Hx | | | | | | | |
| Vitals | x | x | x | | x | x | x |
| Physical Exam | x | x | x | | x | x | x |
| Wound assessments/Photos | x | x | x | | x | x | x |
| Adverse Events, Concomitant Meds | x | x | x | | x | x | x |
| Phone contact to assess for AE | | | | x | | | |
| Pain Assessment | x | x | x | | x | x | x |
| Quality of Life Questionnaire | x | x | x | | x | | x |
| Laboratory testing-Blood[1] | x | x | x | | x | | x |
| Urinalysis | x | x | x | | x | | x |
| PK sample[2] | x | x | | | x | | |
| EB sub-Typing[3] | | | | | | | |
| Blistering and Evaluation[4] | x | x | | | x | x | |
| Confocal Microscopy | x | x | | | x | x | |
| Apply trial medication (COENZYME Q10 3.0% Cream)[5] | x | x | x | | x | x | x |
| Wound care | x | x | x | | x | x | x |
| Dispense trial medication (COENZYME Q10 3.0% Cream)[6] | x | x | x | | x | x | x |
| Instructions to patients | x | x | x | | x | x | x |

[1]Hemoglobin, hematocrit, white blood cell (WBC) count with differential (monocytes, eosinophils, basophils, neutrophils, lymphocytes) as percentage and absolute value, red blood cell (RBC) count, platelet count, and PT/APTT/INR. Albumin, alkaline phosphatase, total bilirubin, bicarbonate/CO2, calcium, cholesterol, chloride, creatinine, creatine kinase, γ-GT, glucose, LDH, inorganic phosphorus, lipase, amylase, magnesium, potassium, total protein, AST, ALT, sodium, triglycerides, urea and uric acid. If the total bilirubin concentration is increased above 1.5 times the upper limit of normal, direct and indirect reacting bilirubin should be differentiated.

[2]PK samples (2 cc) are drawn pre-dosing on Days 1 and 3 of weeks 1 and 8, and 4 hours post dosing on Day 1 of week 1 only.

[3]EB sub typing—if needed.

[4]RCM Evaluation 0, 4, and 48 hours after suction blister procedure.

[5]IP is applied daily to a selected of intact skin and areas of suction blister. To target EB wound, IP is applied every other day to twice a week at the discretion of study team

[6]Caregivers supply dressing materials. Trial medication (CoQ10 3.0% Cream) not applied or dispensed at Wk 12. NOTE: Dressings for the index wound and the suction blister area is provided by the University of Miami.

[7]All patients are seen approximately 4 weeks after the Week 12 visit (around week 16) to assess for any ongoing adverse events.

Screening

Following signed informed consent, obtained in the presence of the investigator or designee, the screening assessments are collected, reviewed, and determined to be acceptable by the Investigator or designee within 14 days before the initiation of study treatment on Day 1. These include date of birth, gender, race, ethnic origin, height, weight, and concurrent diagnoses. In addition, wound assessments and EB sub-typing, if needed, is done (any EB subtyping that has been done in the past is also acceptable—it does not need to be redone). Concomitant Hematology, blood chemistries and urine testing re performed. For female patients of childbearing potential, a urine pregnancy test is performed. Inclusion/exclusion criteria are confirmed. Treatments and other relevant medical and surgical histories as per investigator evaluation are recorded. Vital signs and physical examinations including dermatologic examination of the skin in general are performed. An index wound is selected, photographed and measured.

Baseline/Enrollment

On Week 1, Day 1, patients underwent assessments to re-check and confirm eligibility prior to initiating treatment. Pre-treatment assessment of the selected treatment area, including local skin reactions (LSRs), photos, pigmentation and scarring was performed. Trial medication (CoQ10 3.0% Cream) was dispensed. Scarring was assessed using the Epidermolysis Bullosa Disease Activity and Scarring Index (EBDASI) and the Vancouver Scar Scale, as described in the Journal of the American Academy of Dermatology 2014; 70:89-97, incorporated by reference in its entirety herein.

Trial Treatment Period

The initial application of study treatment was made on Day 1 in the clinic, monitored and guided by clinic staff, to confirm proper application to the lesion(s) as well as the selected intact skin. Thereafter, all study patients (or caregivers) were required to self-apply the study treatment at home, including on trial center visit days. Patients were seen at any time during the study for evaluation of possible adverse events. These were captured as unscheduled visits.

Preparation and Administration of Trial Medication (CoQ10 3.0% Cream)

Trial medication (CoQ10 3.0% Cream) was applied by the patient or caregiver as instructed from every other day to twice per week to wounded skin including the index wound, and every day to a section of intact skin as instructed. At all visits, trial medication (CoQ10 3.0% Cream) and dressings were applied to the index wound and the selection of intact skin at the study center. A small pea size amount of cream was placed on the dominant index finger tip. The trial medication (CoQ10 3.0% Cream) was spread evenly for 5-10 seconds over the selected treatment site and the area surrounding the lesion, so that the total skin area covered with cream was approximately double the size of the treatment lesion. The topical dressing wound was applied to wounded skin with a dressing of patient's or caretaker's choice from the selected list of acceptable topical dressings.

Standard of Care

All patients in all treatment groups received the following standard of care: factors contributing to blistering (such as tightly fitting clothes) were identified and modified; measures were taken to reduce friction to the skin, especially in the areas around index wound and the section of intact skin for suction blister evaluation; the skin was kept clean by gentle cleansing with mild soap and water [but only after 6 hours of trial medication (CoQ10 3.0% Cream) application]; nonabrasive and non-adherent wound dressings were used; a moderately moist lesion environment was maintained by use of specified dressing; for lesions other than the index wound, non-sensitizing antibiotic ointments were used if recommended by the treating physician; and infections were identified and treated promptly.

Trial Outcome Measures

Safety Outcome Analysis: An overall summary of the number (percentage) of patients with any treatment emergent adverse events (TEAEs), SAEs, AEs, LSRs which result in premature discontinuation from treatment or the trial, treatment related AEs, and severe AE were presented.

Efficacy Outcome Analysis: Evaluation of improvement/scarring using the EBDASI Scale as well as an evaluation of improvement of quality of life were presented.

Participant Enrollment and Follow-Up: A total of 10 patients were enrolled and treated with CoQ10 compositions for a maximum of 12 weeks. Patients who remain on trial for 12 weeks were seen for a follow up visit at around Week 16. Patients who had a good response to application of trial medication (CoQ10 3.0% Cream) were given additional supply of study drug, and are followed every six months for any adverse events.

Results of Trial

Case Study #1: 29 Year Old Male with Junctional EB, Non-Herlitz Type

Figure 8A:
FIG. 8A shows a photograph of a target lesion (measuring 15.17 cm) on the lower left anterior leg on Week 1, Day 1, prior to administration of CoQ10 cream.
Figure 8B:
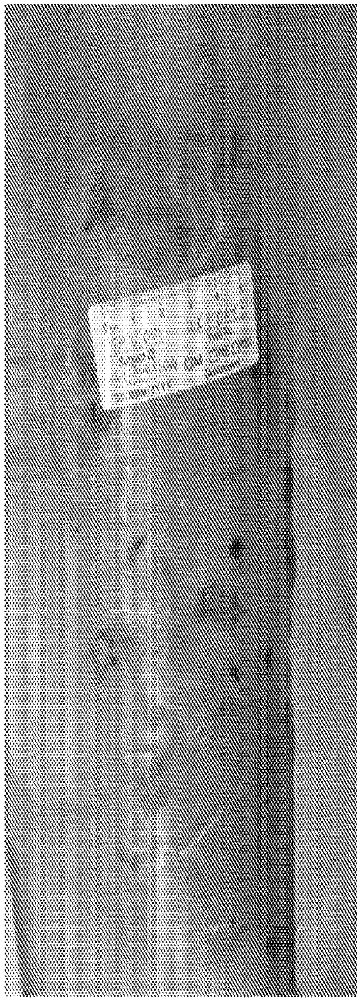
FIG. 8B shows a photograph of the same target lesion (measuring 11.2 cm) on Week 1, Day 3. In addition to size reduction of the lesion, there was a significant diminishment of fluid inside the blister.
Figure 8C:
FIG. 8C shows the target lesion (measuring 9.1 cm) on Week 2, Day 1. The patient in these photographs has Junctional EB, Non-Herlitz sub-type.

The target lesion on Week 1, Day 1, prior to treatment (FIG. 8A), measured 15.17 cm and showed a high degree of erythema. After two applications of the CoQ10 cream, on Week 1, Day 3 (FIG. 8B), the target lesion had decreased to 11.2 cm, and the blisters contained significantly diminished fluid. By Week 2 (FIG. 8C), the target lesion had decreased to 9.1 cm, with further reductions in fluid and swelling.

Case Study #2: 19 Year Old Female with EB Simplex, Dowling Meara Type

Figure 9A:
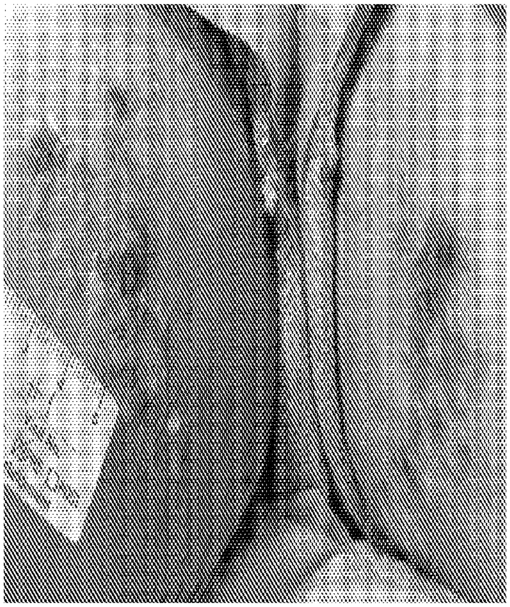
FIG. 9A shows a photograph of a target lesion (measuring 5.28 cm) on the left inner thigh which the patient developed a month prior, on Week 1, Day 1, prior to administration of CoQ10 cream.
Figure 9B:
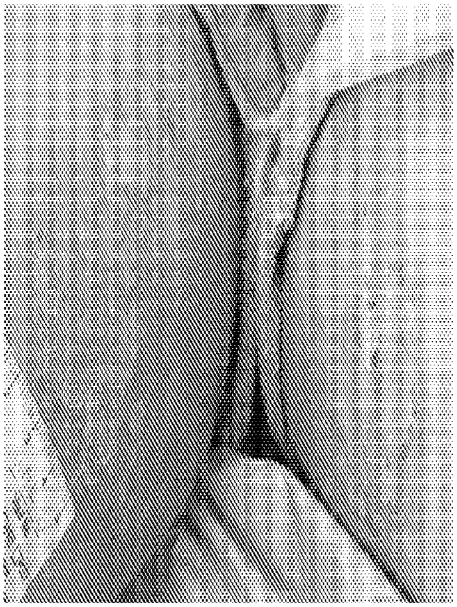
FIG. 9B shows the target lesion (measuring 0.28 cm) on Week 2, Day 1, which shows significant reduction in blistering and three small erosions with granulation present.
Figure 9C:
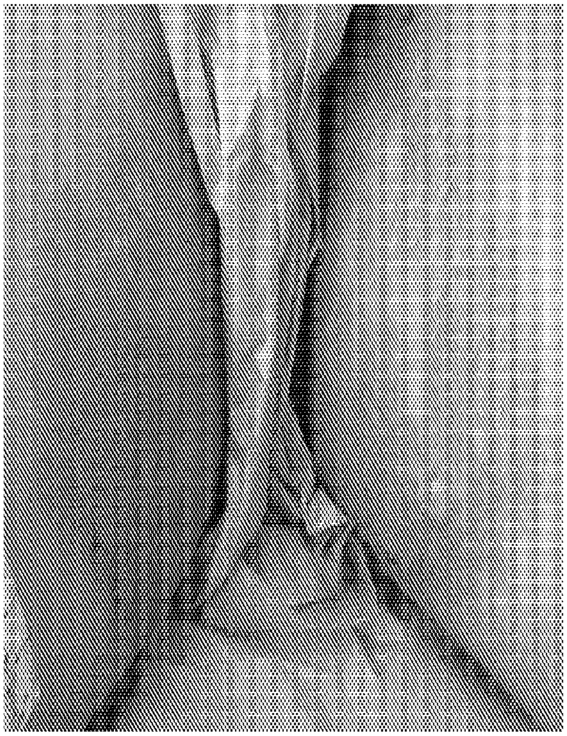
FIG. 9C shows the target lesion (measuring 0.25 cm) on Week 8, Day 1, almost completely re-epithelialized. The patient in these photographs has EB Simplex, Dowling-Meara sub-type.

The target lesion (measuring 5.28 cm, FIG. 9A) on the inner thigh of the subject had been present for a month prior to treatment in the clinical trial. By week 2, the chronic wound had decreased to 0.28 cm (FIG. 9B). At treatment visit Week 8, there was almost complete re-epithelization with only 0.25 cm lesion remaining (FIG. 9C).

Case Study #3: 16 Year Old Female with Junctional EB, Non-Herlitz Type

Figure 10A:
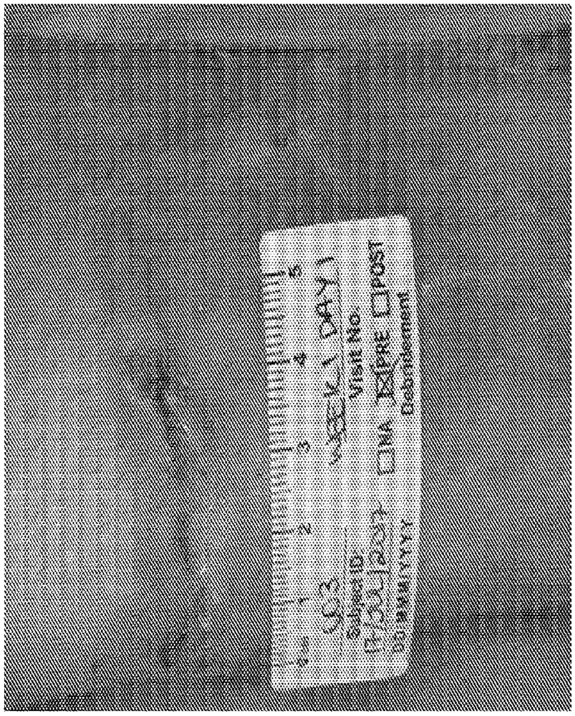
FIG. 10A shows a photograph of a target lesion (measuring 36.96 cm) on the medial lower leg shaft with a main blister with some granulation, on Week 1, Day 1, prior to administration of CoQ10 cream.
Figure 10B:
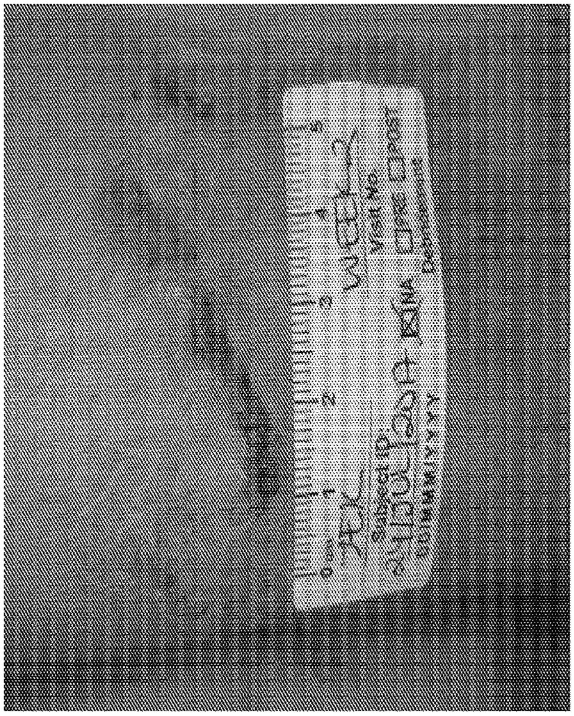
FIG. 10B shows the target lesion (measuring 4 cm) on Week 2, Day 1, with a reduction in blistering and an increase in granulation, with patches of drying.
Figure 10C:
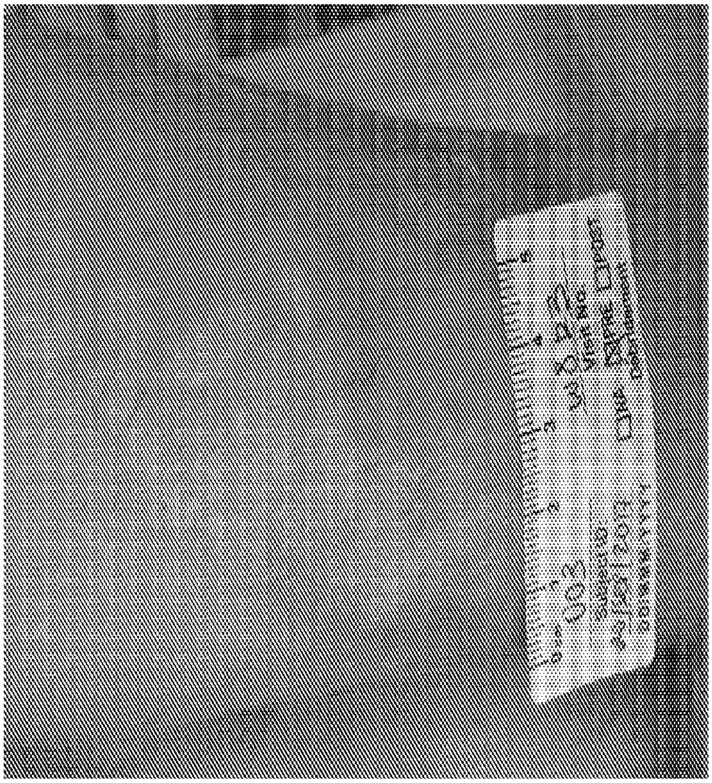
FIG. 10C shows the target lesion (measuring 0 cm) on Week 8, Day 1 with only scarring present. The patient in these photographs has Junctional EB, Non-Herlitz sub-type.

The target lesion on Week 1, Day 1, prior to treatment (FIG. 10A), measured 36.96 cm with some granulation. On Week 2, the lesion showed an increase in granulation and a significant reduction in size to 4 cm (FIG. 10B). By Week 8, the lesion had been completely re-epithelized and only showed scarring (FIG. 10C).

Case Study #4: 17 Year Old Male, Dystrophic EB, Recessive

Figure 11A:
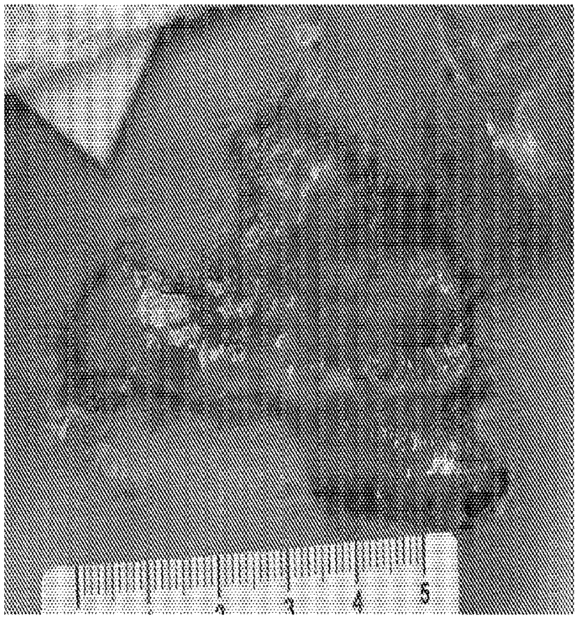
FIG. 11A shows a photograph of a target lesion (measuring 21.76 cm) on the upper right abdomen showing significant exudate and blood with granulation around the border, on Week 1, Day 1, prior to administration of CoQ10 cream.
Figure 11B:
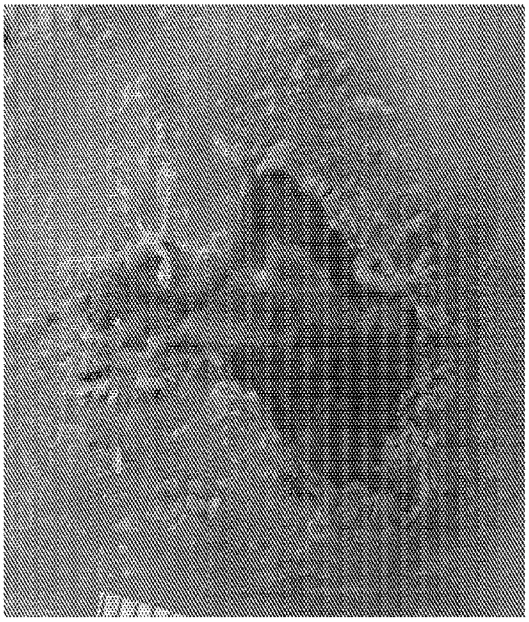
FIG. 11B shows the target lesion (measuring 15.19 cm) on Week 2, Day 1 with greatly increased granulation around the border. The patient in these photographs has recessive, Dystrophic EB.

The target lesion on Week 1, Day 1, prior to treatment, measured 21.76 cm (FIG. 11A) and had significant exudate and blood prior to the first administration of CoQ10 cream. By week 2, the target lesion had shrunk to 15.19 cm and showed significant drying and granulation around the border.

Case Study #5: 59 Year Old Male, Junctional EB

Figure 12A:
FIG. 12A shows a photograph of a target lesion (measuring 20.75 cm) with several granulated erosions on the anterior lower right leg on Week 1, Day 1, prior to administration of CoQ10 cream.
Figure 12B:
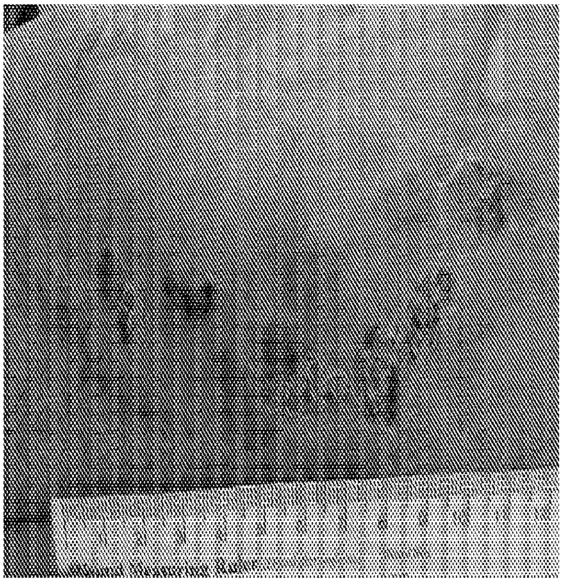
FIG. 12B shows the target lesion (measuring 14.4 cm) on Week 1, Day 3 with a reduction in the number of erosions and significant re-epithelization.
Figure 12C:
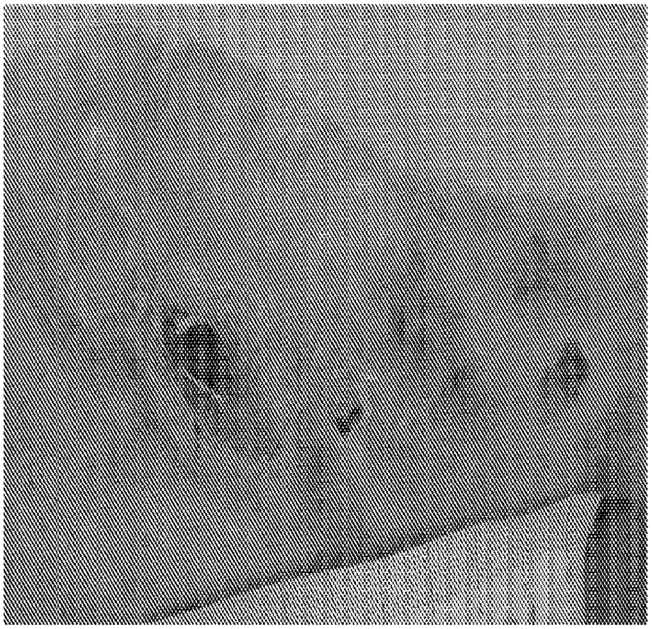
FIG. 12C shows the target lesion on Week 8, Day 1, with a further reduction in the number of erosions, and an increase in re-epithelization. The patient in these photographs has Junctional EB.

The target lesion on Week 1, Day 1, prior to treatment comprised several granulated erosions and measured 20.75 cm (FIG. 12A). On Week 1, Day 3 (following two treatments with the CoQ10 cream), the lesion had decreased in size to 14.4 cm and showed significant re-epithelization (FIG. 12B). By Week 8, the target lesion was significantly healed with further reduction in the number of erosions and more re-epithelization (FIG. 12C).

Conclusions

Topical administration of the 3% CoQ10 cream of the present invention to patients with various forms of EB provides greatly increased healing of blisters and wounds, even chronic wounds which were present for many weeks prior to treatment. Photographs show that profound positive effects—wound closure, blister shrinkage, increase granulation, increase re-epithelization, decreased swelling, and/or decreased blister fluid—were noticeable after even only a few treatments with the composition of the invention. This is in stark contrast to standard of care treatment for EB wounds, which were employed prior to the start of the clinical trial, and clearly did not produce any significant relief.

Example 2. Effect of CoQ10 Compositions on Promoting Healing of Suction Wound Blisters Suction blister test for confocal imaging was also used to evaluate efficacy of CoQ10 3.0% Cream in promoting wound healing when applied to unaffected skin in patients with EB. The rate of reepithelization of suction blister induced at baseline and then at week 8 was compared using reflectance confocal microscopy (RCM) evaluation. The quality of epidermal integrity was assessed using histologic examinations of blister roofs at baseline and week 8. RCM evaluation parameters included features of cutaneous wound repair on a cellular, morphological and architectural level, as well as the documentation of dynamic processes such as blood flow and inflammation, and the successive events of wound healing. All images underwent descriptive morphological analysis.

We evaluated 4 patients 12 years of age and older with confirmed diagnosis of EB. At week 1 day 1 (baseline), we used the CELLUTOME system to create even wounds of 1.8 mm in diameter by suctioning the epidermal layer of intact skin. Clinical and dermoscopy images were taken for all wounds prior to reflectance confocal microscopy (RCM) imaging, which was performed at 0, 4 and 48 hours after wounding. After 48 hours RCM evaluation on week 1, the patients were instructed to apply the CoQ10 3.0% Cream daily to the wound and surrounding area until day 3 of week 8. On week 8 day 1, the CELLUTOME blisters were recreated similarly on the area that has been treated with the topical CoQ10 3.0% Cream. We again performed RCM analysis at 0, 4 and 48 hours of wounding. We captured 6 images at different levels of the wounds during each RCM session. We analyzed all RCM images to describe and compare the cellular and morphological changes during wound healing of the EB patients at baseline (prior to treatment with CoQ10 3.0% Cream) and after 8 weeks of topical CoQ10 3.0% Cream.

Dermoscopy and RCM images show well-defined wounds created by CELLUTOME system on treated skin. In addition, erythema was present and predominant in non-treated wounds (FIGS. 13A, 13C) at 48 hours after wounding, whereas treated wounds had significantly less erythema at baseline and at 48 hours (FIGS. 13B, 13D).

Figure 14A:
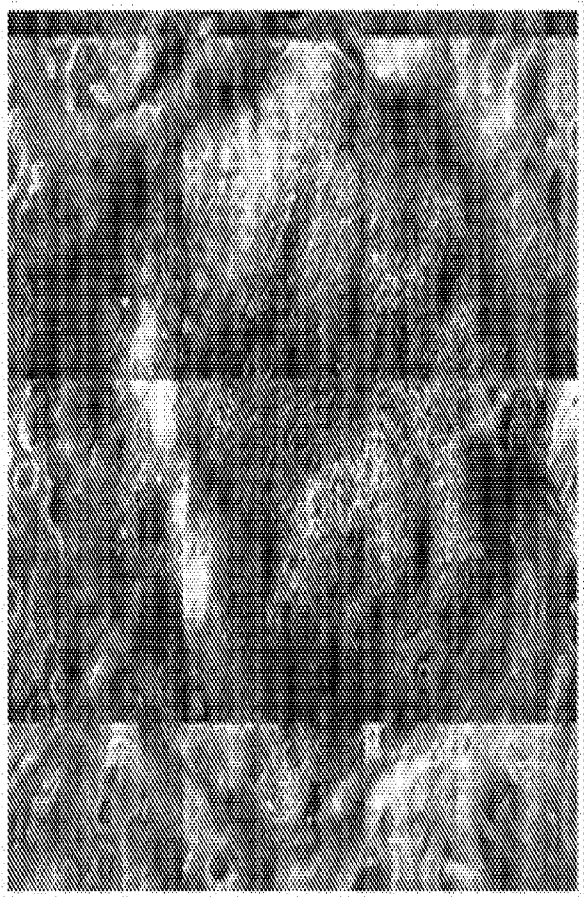
FIG. 14A shows RCM images that were taken at week 1 and FIG. 14B shows RCM images taken at week 8. Diffuse inflammatory cells and disorganized collagen bundles (FIG. 14A) are present at week 1, whereas few inflammatory cells, organized collagen bundles and various corneocytes are seen at week 8 (FIG. 14B).
Figure 14B:
Figure 15A:
FIG. 15A shows RCM images that were taken at week 1.
Figure 15B:
FIG. 15B shows RCM images taken at week 8. Granular tissue covers the wound with large corneocytes at week 8 (FIG. 15B), whereas inflammatory cells with some areas with granular tissue is seen at week 1 (FIG. 15A).
Figure 16A:
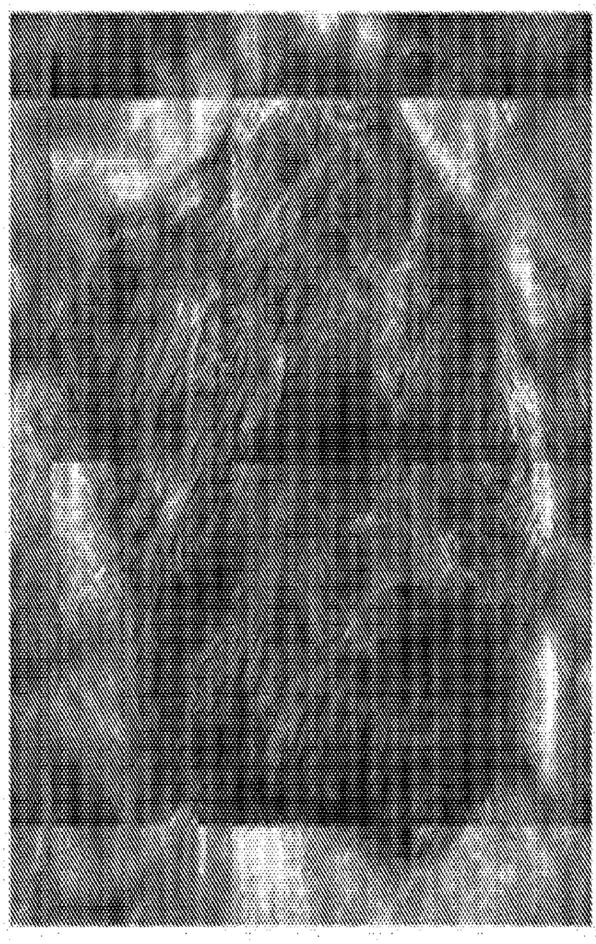
FIG. 16A shows RCM images that were taken at week 1.
Figure 16B:
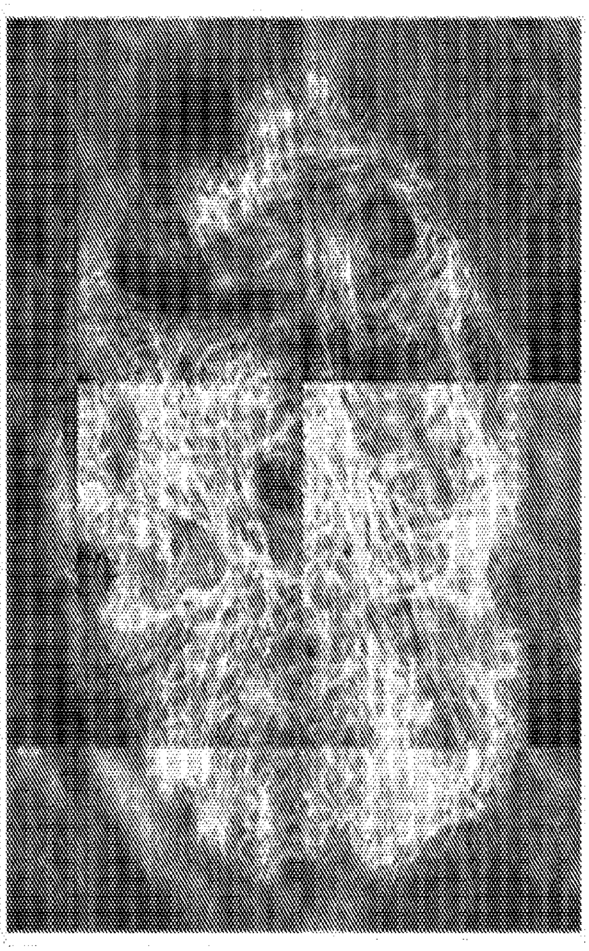
FIG. 16B shows RCM images taken at week 8. Thicker collagen bundles are present at week 8 (FIG. 16B), whereas thin collagen bundles are present at week 1 (FIG. 16A).

In the non-treated (baseline) wounds, RCM images show collagen bundles and diffuse inflammatory cells that persisted at 48 hours after wounding (FIG. 14A). Additionally, we also observed granular tissue and few polygonal corneocytes (FIG. 14A). In contrast, there were significantly few inflammatory cells after treatment (FIG. 14B). Moreover, we saw organized collagen bundles and various corneocytes at week 8 (FIG. 14B), which is strong evidence of advancing healing. Treatment lead to significant collagen production and organization, as shown in the RCM images showing thin bundles (FIG. 16A) on untreated skin versus the thicker and more organized bundles of collagen present after treatment (FIG. 16B). Furthermore, there were stark differences in the amount of inflammatory cells and granulation seen between untreated skin (FIG. 15A) and treated skin (FIG. 15B). In treated skin, inflammatory cells were present 4 hours after wounding, but had significantly decreased at 48 hours. Additionally, extensive granular tissue and several polygonal corneocytes were present 48 hours after wounding (FIG. 15B).

Patients also reported better healing while applying CoQ10 3.0% Cream. The patient images discussed above show that CoQ10 3.0% Cream improve skin integrity in EB patients. The CoQ10 3.0% Cream also was shown to decrease the inflammatory wound healing stage and increase components of the proliferative stage, which will lead to a successful healing in EB patients. No adverse reaction to the CoQ10 3.0% Cream was reported.

Example 3. Effect of COQ10 Compositions on Structural Proteins

Wound healing requires a combination of the deposition of new connective tissue matrix i.e. granulation tissue, and wound contraction requires multiple cell types including fibroblasts and keratinocytes. Both of these cell types produce many structural proteins that are critical for re-epithelialization and remodeling of the wound area to complete the process of healing. Thus, agents with ability to modulate expression of key components of the extracellular matrix will potentially improve tissue regeneration and facilitate wound healing. Treatment of fibroblasts and keratinocytes with CoQ10 compositions was found to be associated with changes in the expression of various structural proteins. Treatment with CoQ10 compositions in fibroblasts influenced the expression of various structural protein including collagens, plectin, annexins, vimentin, filamins and laminins, all of which have been implicated in the various pathologies associated with EB. Similarly, keratinocytes treated with CoQ10 compositions demonstrated changes in expression of structural proteins including several keratins including KRT13, KRT14 and KRT17 respectively. The ability of CoQ10 compositions to influence expression of structural proteins that are involved in maintenance of skin structure and function, along with its ability to influence critical phases of wound healing process provides compelling rationale for its utility in treatment of wounds in EB.

Example 4. Use of CoQ10 Compositions for Treating Cutaneous Squamous Cell Carcinoma in Subjects with Epidermolysis Bullosa In addition to the debilitating injuries to epithelial tissues in various organs, patients with EB encounter other complications including growth retardation, anemia, muscular dystrophy and deformities of hands and feet. However, the cause of morbidity and mortality in adults with EB is related to the incidence of malignancies, of which cutaneous squamous cell carcinoma (cSCC) is very significant.

The incidence of cutaneous SCC is predominant in recessive dystrophic EB (RDEB) patients, with cumulative risk reaching 67.8%, 80.2% and 90.15 by ages 35, 45 and 55 years respectively during lifetimes. The incidence rates in EB are significantly higher compared to lifetime risk of cutaneous SCC in non-EB patients in the United States, at 7-11% in the Caucasian population. In addition, almost 80% of EB patients die of metastatic SCC in spite of aggressive surgical interventions. Incidence of cSCC is also observed in the junctional EB (JEB) patient population, where the lifetime cumulative risk is approximately 18.2% at 25 years of age.

The higher incidence combined with the aggressiveness of cutaneous SCC observed in EB patients compared to non-EB patients suggests differences in the molecular etiopathology of cSCC. Molecular markers including mutations in p53, expression variations in matrix metalloproteinases (MMPs), cyclin dependent kinases (CDKs) and melanocortin 1 receptor (MC1R) polymorphisms have been established as major determinants in the initiation and progression of cSCC. In contrast, there is a lack of consistent evidence implicating a particular pathway in the etiology of cSCC in EB patients. Numerous factors including tissue stress (due to EB associated defects in wound healing), premalignant potential of keratinocytes due to EB associated mutations, growth factors and other diminished immune surveillance have been suggested as major players in the onset/progression of cSCC in EB patients. Molecular analysis has identified regulators of apoptosis (e.g. p53), growth factors (e.g. EGFR, FGF), proteases (MMPs, Collagenase) and epigenetics (HDACs) in the incidence and progression of cSCC in EB patients.

Of interest is the observation that keratins (e.g. KRT6, KRT16, KRT17) and MMPs (1, 3, 9, 10) were most robustly modulated in cSCC in kidney transplant patients. Given that aberrations in structural proteins like collagen (e.g. Col7A, Col17), keratins (e.g. KRT5, KRT14) and laminins (e.g. laminin 5) have been associated with EB, and that proteases such as MMPs (1, 2, 3, 5, 9) and collagenase are associated with cSCC in both EB and transplant patients, it is thought that that the intersection of molecular networks encumbering cytoskeletal structural proteins and protease activities in combination with cell cycle regulation and apoptosis most likely influence the initiation and progression of cSCC in EB patients.

To date, there does not appear to be any standard criteria for defining or management of these patients. Surgical resection, chemotherapy and/or radiation are the three modalities of standard of care with significant variability in responses and long-term outcomes. Both chemotherapy and radiation use is associated with significant incidences of adverse effects. There are currently very limited therapeutic options available for treatment of cSCC in recessive dystrophic epidermolysis bullosa (RDEB) patients.

The tumor suppressor p53 is considered the guardian of the genome and regulates DNA repair mechanisms to avoid activation of apoptotic pathways to eliminate the damaged keratinocytes. In the epidermis, internal/external insults with the potential to induce DNA damage (e.g. UV exposure) results in the activation of p53, orchestrating DNA repair if possible or committing cells to undergo apoptosis if DNA damage is beyond repair (Ortonne, 2002). In addition, p53 itself may be a direct target of insult/injury/stress, and loss of function p53 can result in uncontrolled proliferation and loss of apoptotic function. Mutation in p53 is frequently observed in skin cancers, and its frequency in various skin cancers is highly variable (Einspahr et al, 1999).

Etiology of SCC as a consequence of high cumulative sun exposure has been the primary area of research due to incidence and morbidity/mortality in the Caucasian population. In addition to patients with EB, higher incidence of SCC has also observed in patients receiving immunosuppressive therapy, augmented during infection with human papilloma virus infection (Pons et al, 2006). Actinic keratosis and SCC in-situ are the pre-invasive stages of invasive SCC. Mutations in p53 have been identified in greater than 60% of SCC and AK and such mutation is characteristic of that induced by UV radiation (Pons et al, 2006). In addition to loss of heterozygosity (LOH) at the p53 locus (17 p.13.1), other chromosomes carrying LOH have been characterized (Boukamp, 2005). Other factors including inflammation (e.g. TNF-alpha, IL-6), lipid peroxidation, reactive oxygen species and mitochondrial DNA damage have been implicated in the onset and progression of SCC (Bachelor et al, 2009). There is general consensus that multiple genetic, physiological and microenvironmental factors contribute to the spread and aggressiveness of SCC.

A tissue specific insult (i.e. UV induced cell damage in AK/BCC) can be considered as an “initiation” step in the process of oncogenesis, but is insufficient for the neoplastic lesions to acquire malignancy. Clonal expansion of these neoplastic lesions in combination with global genetic, proteomic and phenotypic alteration is essential for acquisition of malignant phenotype and metastatic potential. Starting with the classical studies by Otto Warburg it is now well established that metabolic transformation in the neoplastic lesion is essential and necessary for acquisition of malignant capabilities. This is evidenced by highly proliferative tumors that exhibit the Warburg phenotype utilizing glucose as the primary source of generating ATP in the cytoplasm and circumventing mitochondrial oxidative phosphorylation (Weinhouse, 1956, Burk et al, 1956). Given that AK and BCC are associated with low-grade malignancy and the extended duration of latency (several decades) required for onset of malignant phenotype, this suggests presence of oncogenic enabling insult in the absence of metabolic switch. In contrast, transition of AK to SCC in-situ is associated with slow yet progressive clonal expansion of the neoplastic lesion along with changes in gene, protein and metabolic signatures characteristic of malignant phenotype (Berhane, 2002). This might also involve inflammatory factors evidence by the efficacy of Aldara that specifically targets Toll-like receptor, the use of which is associated with incidence of significant side effects. Multiple strategies aimed at circumventing cellular bioenergetics networks driving utilization of glucose to generate ATP have been investigated as potential therapies for cancers (Yeluri et al, 2009). Highly proliferative cancers such as metastatic SCC and melanoma are characterized by metabolic phenotype that is essential for maintenance of their malignant capabilities (Scatena et al, 2011; Hersey et al, 2009). A novel Coenzyme Q10 containing formulation was developed as a means to selectively influence cellular bioenergetics pathways in cancer without influencing functions in normal cells. CoQ10 is an integral component of the mitochondrial electron transfer chain for the production of adenosine triphosphate (ATP), the primary energy source of the cell. It addition to its role in energy metabolism, CoQ10 functions as an antioxidant, membrane stabilizer, and free-radical scavenger. CoQ10 formulations have been investigated as a treatment for oncologic, cardiac, neurologic, metabolic, and genetic disorders. Coenzyme Q10 specifically targets cellular bioenergetics networks shifting energy production from the cytoplasm (observed in highly metabolically active, proliferative cancers) towards mitochondrial oxidative phosphorylation (observed in normal tissues).

International Application No. PCT/US2005/001581, incorporated by reference in its entirety herein, describes topical formulations of CoQ10 that reduce the rate of tumor growth in an animal subject.

In-vitro studies with CoQ10 demonstrate its ability to selectively influence the viability of cancer cells in the absence of overt toxicity in normal cells. FIG. 1 describes the dose dependent decrease in cell proliferation rates of squamous cell carcinoma and melanoma cell lines, but no effect on normal human keratinocytes and fibroblasts.

The concentration dependent decrease in the cell proliferation rates observed for melanoma (SK-MEL-28) and squamous cell carcinoma (SCC-25) cell lines is indicative of Coenzyme Q10 in selectively influencing cancer cells without toxicity in normal cell lines (i.e. normal human keratinocytes and adult fibroblasts). When applied topically to melanoma tumors in nude mice, a 1.0% CoQ10 formulation inhibited growth and angiogenesis. The mechanism involves the shifting of the cellular bioenergetics from cytoplasmic glycolysis towards mitochondrial oxidative phosphorylation (AACR 2011). The shift in cellular metabolic pathways in cancer including SCC and melanoma results in the recapitulation of the p53 regulated apoptotic potential by re-establishing the balance of pro-apoptic Bcl-2/Bax ratios in a manner conducive for cell death.

Figure 2A:
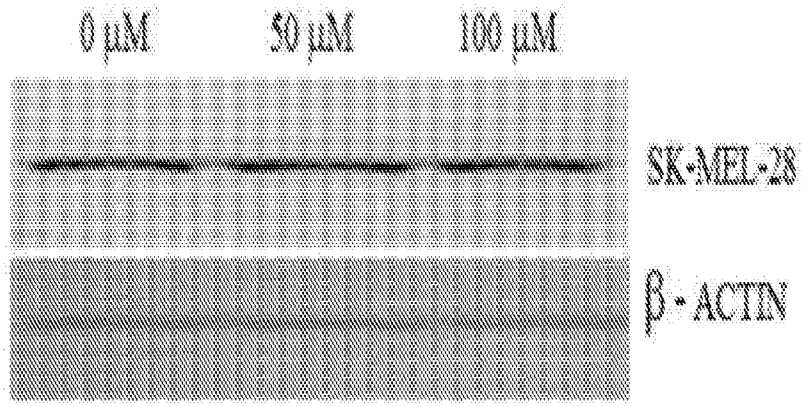
FIG. 2A and FIG. 2B show the expression of isocitrate dehydrogenase (IDH-1) in SK-MEL-28 melanoma cells treated with increasing concentration of Coenzyme Q10 (50 μM or 100 μM).
Figure 2B:
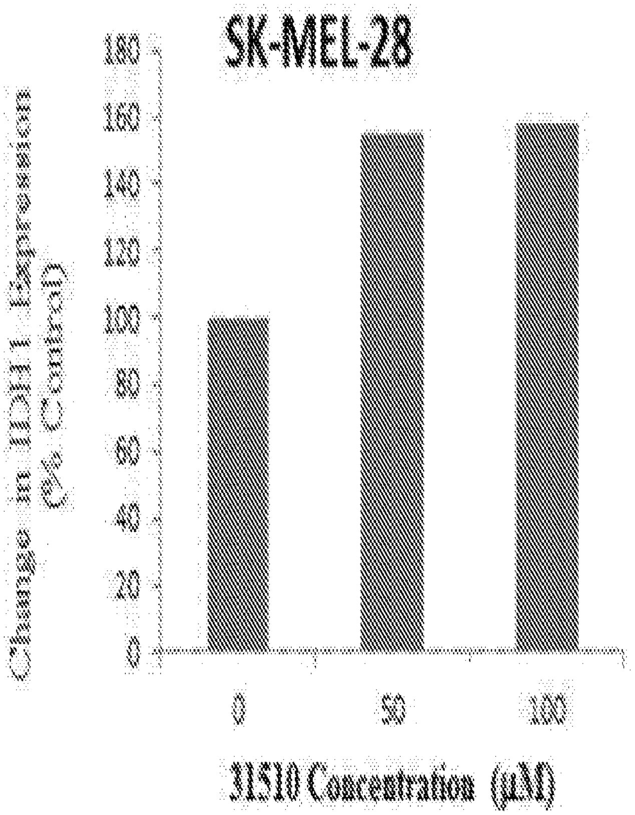

Isocitrate dehydrogenases (IDH-1 and IDH-2) are NADP+-dependent enzymes that catalyze the oxidative decarboxylation of isocitrate to a-ketoglutarate. IDH-1 is the cytosolic isoform mutation which is associated with incidence of brain cancer in humans (Parsons et al, 2008). Furthermore, expression of mutated IDH-1 associated with dysfunctional enzyme is associated with increased expression of Hif-1a (Zhao S et al, 2009). Dysfunctional IDH enzyme is associated with incidence of various cancers, suggesting that an increase in expression of normal IDH enzyme should be associated with recapitulation of normal oxidative phosphorylation. Treatment with Coenzyme Q10 in melanoma cells is associated with a concentration dependent increase in expression of IDH-1 (FIG. 2), suggesting an increase in mitochondrial oxidative phosphorylation.

Figure 3A:
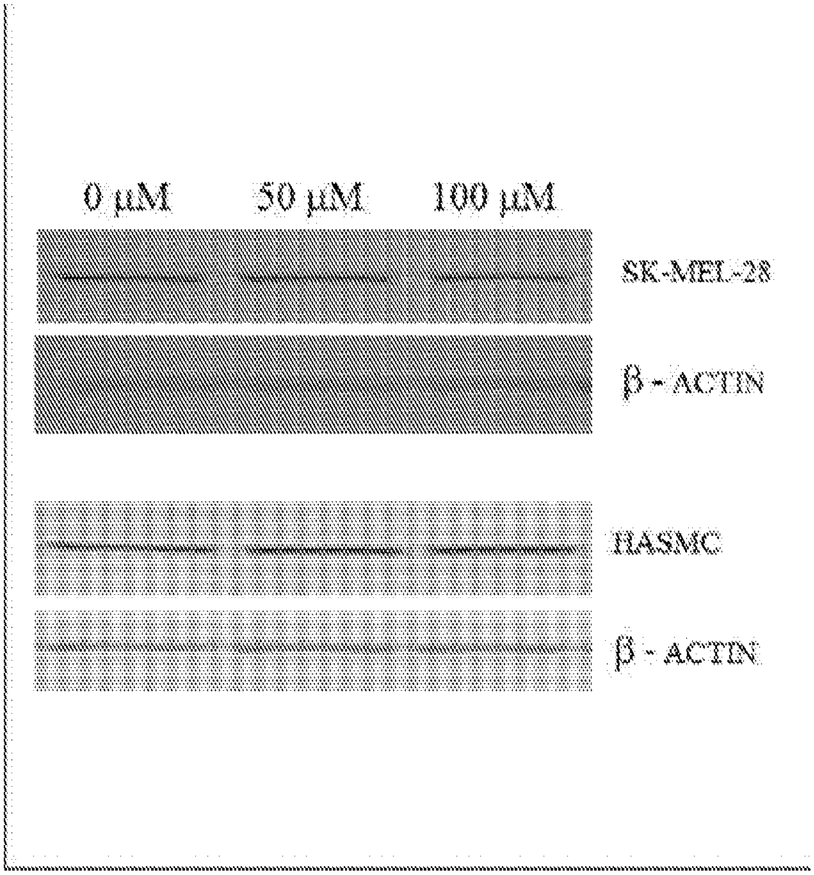
FIG. 3A and FIG. 3B show the effect of Coenzyme Q10 treatment (50 μM or 100 μM) on expression of ATP Citrate lyase (ACL) in SK-MEL-28 melanoma cells. Human aortic smooth muscle cells (HASMC) were used as a control.
Figure 3B:
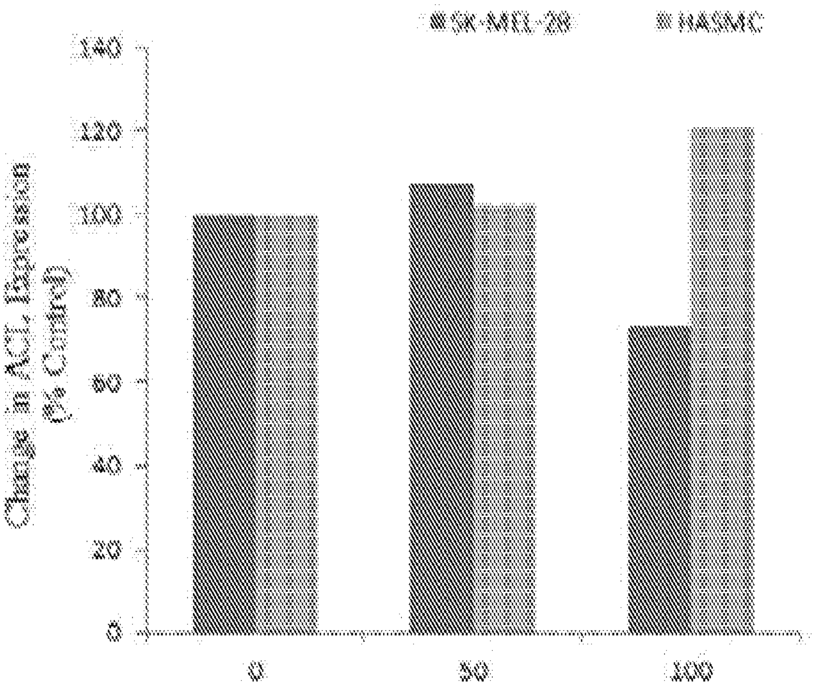

ATP citrate lyase (ACL) is the primary enzyme responsible for the conversion of glucose derived cytosolic citrate into acetyl-CoA for the biosynthesis of lipids and cholesterol (Bauer et al, 2005). In addition, the ATP-citrate lyase generated acetyl-CoA is essential for histone acetylation in response to growth factor stimulation and during differentiation (Wellen K E et al, 2009). It has been suggested that a decrease in ACL activity may be associated with increased oxidation of citrate in the mitochondria, resulting in increased TCA cycle activities and oxidative phosphorylation (Board M and Newsholme E, 1996). Thus, the Coenzyme Q10 induced decrease in ACL expression in a melanoma cell line (FIG. 3) suggests a decrease in lipid and cholesterol biosynthesis essential for proliferation and acetylation of histones in the regulation of transcriptional activities associated with cancer cell growth and differentiation. A similar decrease in ACL expression is not observed in normal (HASMC) cells in response to Coenzyme Q10 treatment. Thus, treatment of cancer cells with Coenzyme Q10 alters expression of proteins in a manner consistent with augmentation of mitochondrial oxidative phosphorylation, with associated decreases in pathways essential for sustained proliferation.

Figure 4A:
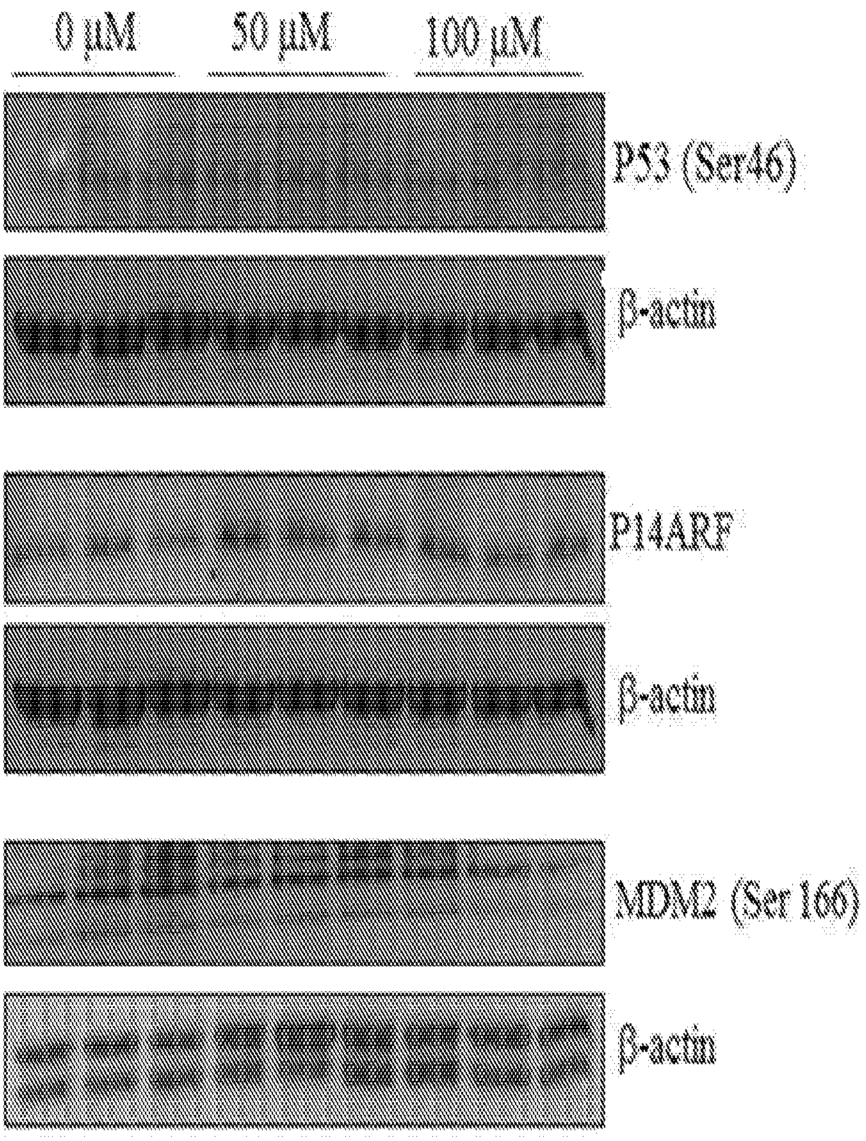
FIG. 4A and FIG. 4B show the effect of Coenzyme Q10 on expression of p53, pl4ARF and MDM2 in SK-MEL-28 melanoma cells.
Figure 4B:
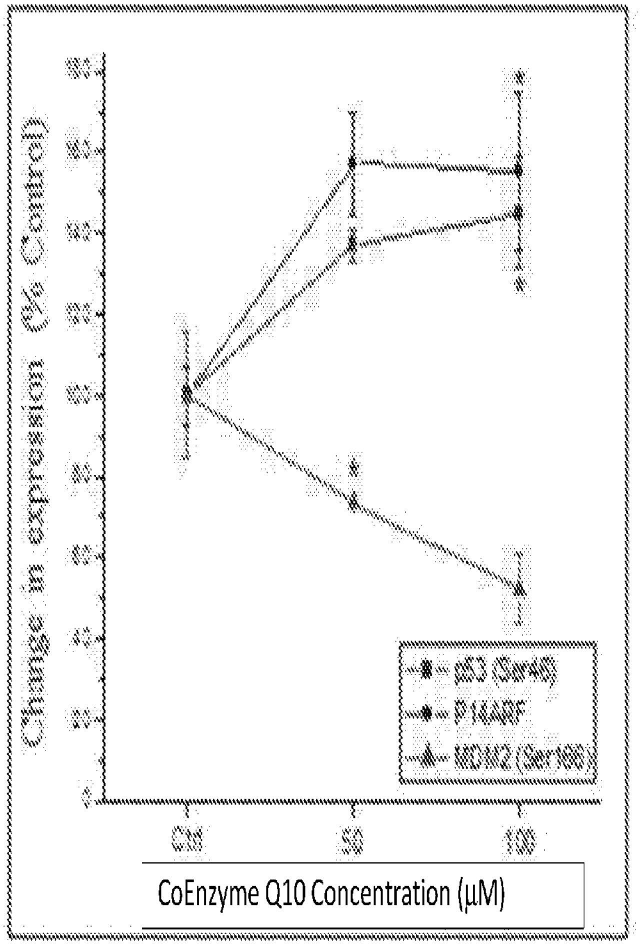

In another set of experiments, treatment of melanoma cells (SK-MEL-28) with the CoQ10 compositions resulted in a concentration dependent progressive increase in levels of p53 and p14ARF, which are known to regulate apoptotic pathways. MDM2 is a negative regulator of p53 expression and activity, and thus the decrease in expression shown in FIG. 4 represents an indirect validation of the increase in p53 expression in response to Coenzyme Q10 treatment.

Figure 5:
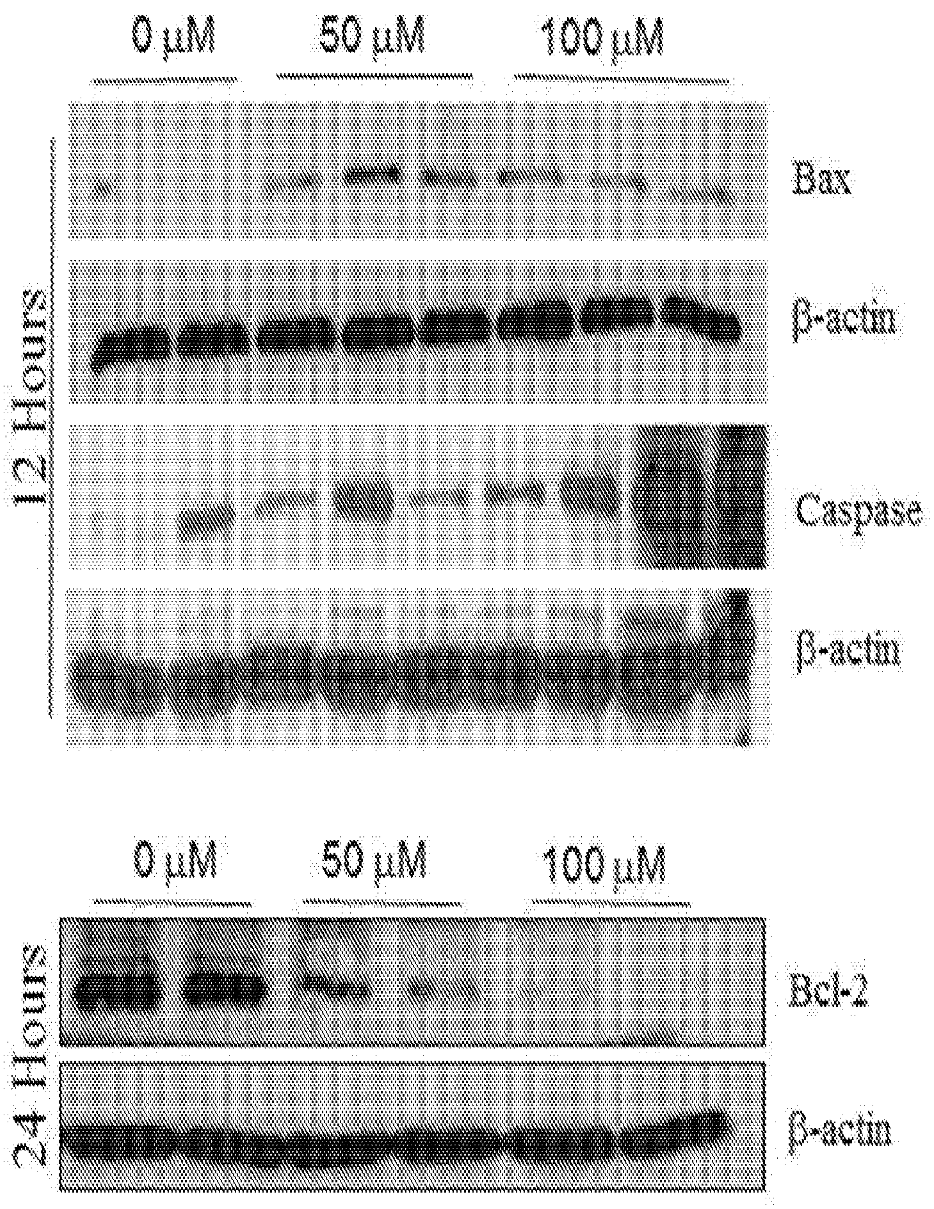
FIG. 5 is a Western Blot that shows the change in expression of Bcl-2, Bax and Caspase 3 in SK-MEL-28 cells in response to Coenzyme Q10 exposure (50 μM or 100 μM) for 12 or 24 hours. Bcl-2, Bax and Caspase 3 are pro- and anti-apoptotic markers regulating cell death pathways. A beta-actin loading control was used. A concentration dependent decrease in anti-apoptotic bcl-2 protein was observed following exposure to Coenzyme Q10, and a concentration dependent increase in expression of pro-apoptotic bax was observed following exposure to Coenzyme Q10.

FIG. 5 describes the expression of pro- and anti-apoptotic markers regulating cell death pathways in a melanoma cell line. A concentration dependent decrease in anti-apoptotic bcl-2 protein with a concomitant increase in expression of pro-apoptotic bax is observed following exposure to Coenzyme Q10. The progressive dose-dependent increase in expression of caspase 3, an executioner caspase, is indicative of the ability of Coenzyme Q10 to enable commitment of the cancer cells to the process of apoptosis.

Next, a proteomic analysis of an in-vitro model of squamous cell carcinoma, SCC cell line (SCC-25), was undertaken to delineate the underlying mechanistic regulating effect of the CoQ10 compositions of the invention. Table 1, shown above and reproduced below, lists the proteins identified to have a differential response to 100 uM CoQ10 treatment in SCC cells at 6 and 24 hours.

TABLE 2

| Protein | Name | Response (fold change) |
|---|---|---|
| Transaldolase 1 | TALDO1 | Decrease (1.5) at 6 and 24 hr |
| NM23 protein | NME1 | increase (−1.2) at 6 hr, decrease at 24 hr |
| Heat shock 27 kDa protein 1 | HSPB1 | Increase (−1.9) at 6 and 24 hr |
| Keratin 1 | KRT1 | Decrease (2.3) at 6 and 24 hr |
| Keratin 14 | KRT14 | Increase (−1.6) at 6 and 24 hr |
| Keratin 13 | KRT13 | Increase (−1.5) at 6 and 24 hr |
| Protessome Beta 7 | PSMB7 | Decrease (1.6) at 24 hr only |
| Proteasome activator subunit 3 | PSME3 | Decrease (1.3) at 24 hr only |
| Rho GDP dissociation inhibitor (GDI) alpha | ARHGDIA | Decrease (1.5) at 6 hr only |

In the SCC model, treatment with CoQ10 was associated with a decrease in Transaldolase-1, an enzyme within the pentose phosphate pathway that regulates biosynthesis of intermediates for nucleic acids. Furthermore, Transaldolase-1 is also involved in maintenance of cellular reducing equivalent (NADPH) balance and glutathione based redox status. In addition, CoQ10 exposure in SCC was associated with changes in expression of stress proteins & keratins. A deficit in keratin 14 has been documented in EB, one of the keratins the expression of which is increased in response to the CoQ10 composition in the SCC model.

Table 3, shown above and reproduced below, lists the genes in SCC cells that are regulated by 100 uM Q10 treatment when analyzed by the Apoptosis Array.

TABLE 3

| Symbol | Description | Regulation. |
|---|---|---|
| AKT1 | V-akt murine thymoma viral oncogene homolog 1 | Down regulated at 6 hours and then up regulated at 24 hours. |
| BAG4 | BCL2-associated athanogene 4 | Up regulated at 24 hours. |
| BAX | BCL2-associated X protein | Up regulated at 24 hours. |
| BCL2L1 | BCL2-like 1 | Down regulated at 6 hours and then up regulated at 24 hours. |
| BNIP3 | BCL2/adenovirus E1B 19 kDa interacting protein 3 | Down regulated at 24 hours. |
| CARD6 | Caspase recruitment domain family, member 6 | Down regulated at 6 hours. |
| CASP6 | Caspase 6, apoptosis-related cysteine peptidase | Up regulated at 24 hours. |
| CASP7 | Caspase 7, apoptosis-related cysteine peptidase | Up regulated at 24 hours. |
| GADD45A | Growth arrest and DNA-damage-inducible, alpha | Up regulated at 24 hours. |
| TP53 | Tumor protein p53 | Up regulated at 24 hours. |
| TP73 | Tumor protein p73 | Down regulated at 6 hours and then up regulated at 24 hours. |

Analysis of changes in transcriptional expression in SCC cells in response to CoQ10 exposure was associated with a sustained increase in p53 transcripts over 24 hours. In contrast, there was an initial decrease followed by an increase in TP73 transcripts. Other major changes observed in SCC cell lines in response to CoQ10 treatment were a decrease in AKT1 in tandem with upregulation of pro-apoptotic markers, including Bax and multiple caspases. Collectively, the data from Table 1 and Table 2 suggests that CoQ10 exposure in SCC cell lines is associated with changes in metabolic phenotype, activation of p53 and apoptosis.

Numerous in-vitro and in-vivo studies provide support for the ability of CoQ10 to shift cellular bioenergetics to facilitate ATP synthesis via mitochondrial oxidative phosphorylation. The consequences of the shifting cellular bioenergetics from glycolysis towards oxidative phosphorylation induced by Coenzyme Q10 are the alterations in apoptosis, angiogenesis, mitochondrial and nuclear function in selectively targeting cancer cells to undergo cell death in the absence of toxicity in normal cells.

The results provided herein demonstrate that Coenzyme Q10 is a molecule with the ability to selectively interfere with the cancer metabolic network, shifting the dependence of cancer in the direct utilization of glucose to generate ATP toward pathways supporting mitochondrial oxidative phosphorylation. Coenzyme Q10 exposure associated shifts in the cellular bioenergetics utilization network towards mitochondrial oxidative phosphorylation is linked to recapitulation (correction) of p53 mediated apoptotic pathways that have gone awry in cancer cells. The activity and mechanism of action of Coenzyme Q10 clearly demonstrates its utility in the efficacious treatment of metastatic SCC characterized by high metabolic activity observed in a bona-fide oncogenic environment.

In summary, the results provided herein support the potential utility of the Coenzyme Q10 composition, which comprises CoQ10 in a proprietary lipid nanodispersion with penetration enhancers, to facilitate significant uptake in target tissues for the treatment of SCC in general, and in treatment of the aggressive cSCC observed in EB patients.

REFERENCES

Alessi S S, Sanches J A, de Oliveira W R, Messina M C, Pimentel E R, FestaNeto C. Treatment of cutaneous tumors with topical 5% imiquimod cream. Clinics (Sao Paulo). 2009; 64(10):961-6.

Altintas M A, Altintas A A, Knobloch K, Guggenheim M, Zweifel C J, Vogt P M. Differentiation of superficial-partial vs. deep-partial thickness burn injuries in vivo by confocal-laser-scanning microscopy. Burns. February 2009; 35(1):80-86.

Anonymous. Imiquimod for superficial and in situ skin malignancy. Drug Ther Bull. 2009; 47(10):113-6.

Ashton G H. Kindler's syndrome. Clin Exp Dermatol 2004; 29:116-21.

Bargman H, Hochman J. Topical treatment of Bowen's disease with 5-Fluorouracil. J Cutan Med Surg. 2003; 7(2):101-5.

Bernhard J D, Elliot A D. A Letter From Darier to Bowen on the Naming of Bowen's Disease. Arch Dermatol. 1983; 119(3):261-262. doi:10.1001/archderm.19831650270079021

Braathen L R, Szeimies R M, Basset-Seguin N, et al. Guidelines on the use of photodynamic therapy for non-melanoma skin cancer: an international consensus. International Society for Photodynamic Therapy in Dermatology, 2005. J Am Acad Dermatol. 2007; 56(1):125-43.

Cepeda-Valdés R, et al. Actas Dermosifiliogr 2010; 101: 673-82.

Chipperfield B. Ubiquinone concentrations in some tumour-bearing tissues. Ubiquinone concentrations in tumors and some normal tissues in man. Nature. 1966; 209(29): 1207-8

Chute C G, Chuang T Y, Bergstralh E J, Su W P. The subsequent risk of internal cancer with Bowen's disease. A population-based study. JAMA. 1991; 266(6):816-9.

D'Alessio et al., J Invest Dermatol 2008; 128:2815-9.

Declaration of Helsinki—1996 version; last revised 2008 (Seoul).

Demidova-Rice T N, Hamblin M R, Herman I M. [Acute and impaired wound healing: pathophysiology and current methods for drug delivery, part 1: normal and chronic wounds: biology, causes, and approaches to care]. Adv. Skin Wound Care. 2012; 25(7):304-14.

Derancourt C, Mougin C, ChopardLallier M, Coumes-Marquet S, Drobacheff C, Laurent R. [Oncogenic human papillomaviruses in extra-genital Bowen disease revealed by in situ hybridization]. Ann Dermatol Venereol. 2001; 128(6-7):715-8.

Drake A L, Walling H W. Variations in presentation of squamous cell carcinoma in situ (Bowen's disease) in immunocompromised patients. J Am Acad Dermatol. 2008; 59(1):68-71.

Dupree M T, Kiteley R A, Weismantle K, Panos R, Johnstone P A. Radiation therapy for Bowen's disease: lessons for lesions of the lower extremity. J Am Acad Dermatol. 2001; 45(3):401-4.

Fiechtinger R G, Sperl W, Bauer J W, Kofler B. Mitochondrial dysfunction: a neglected component of skin diseases. Experimental Dermatology. 2014; 23(9):607-614.

Fine J D. In Schachner L A (ed). Pediatric Dermatology. Churchill-Livingstone Inc. 1995; pag. 767-809.

Fine et al., J Am Acad Dermatol 2008; 58:931-50.

Fine J D. Inherited epidermolysis bullosa. p. 435. In Fine J D (ed): Bullous Diseases. Igaku-Shoin, New York, 1993.

Fine J D. Inherited epidermolysis bullosa. Orphanet J Rare Dis 2010; 5:12.

Folkers K, Osterborg A, Nylander M, Morita M, Mellstedt H. Activities of vitamin Q10 in animal models and a serious deficiency in patients with cancer. Biochem Biophys Res Commun. 1997; 234(2):296-9

Fulton J E Jr, Carter D M, Hurley H J. Treatment of Bowen's disease with topical 5-fluorouracil under occlusion. Arch Dermatol. 1968; 97(2):178-80.

Guo S, Dipietro L A. Factors affecting wound healing. J. Dent. Res. 2010; 89(3):219-229.

Gupta S, Nutan, Dogra S, Kanwar A J. Bowen Disease over photo protected site in an Indian male. Dermatol Online J. 2009; 15(10):16.

Gupta A, Raghubir R. Energy metabolism in the granulation tissue of diabetic rats during cutaneous wound healing. Mol Cell Biochem. 2005; 270: 71-77.

Hanna W, Silverman E, Boxall L, Krafchik B R. Ultrastructural features of epidermolysis bullosa. Ultrastruct Pathol 1983; 5: 29-36.

Hintner H, Stingi G, Schuler G, et al. Immunofluorescence mapping of antigenic determinants within the dermal-epidermal junction in the mechano-bullous diseases. J Invest Dermatol 1981; 76: 113-118.

Im M J, Hoopes J E. Energy metabolism in healing skin wounds. J Surg Res 1970; 10:459-464.

Ishe 1993 Ihse I, Andren-Sandberg, Nylander M, Folkers K. Research on a deficiency of coenzyme Q10 (Coenzyme Q10) in cancer patients. And initiation of treatment with Coenzyme Q10. 8th Int. Symp Biomed and Clin. Aspects of Coenzyme Q, 1993, p. 48.

Jones C M, Mang T, Cooper M, Wilson B D, Stoll H L Jr. Photodynamic therapy in the treatment of Bowen's disease. J Am Acad Dermatol. 1992; 27(6 Pt 1):979-82.

Keast et al. Wound Repair Regen 2004; 12(3 Suppl): S1-17.

Kossard S, Rosen R. Cutaneous Bowen's disease. An analysis of 1001 cases according to age, sex, and site. J Am Acad Dermatol. 1992; 27(3):406-10.

Kovács A, Yonemoto K, Katsuoka K, Nishiyama S, Harhai I. Bowen's disease: statistical study of a 10 year period. J Dermatol. 1996; 23(4):267-74.
Lange-Asschenfeldt S, Bob A, Terhorst D, et al. Applicability of confocal laser scanning microscopy for evaluation and monitoring of cutaneous wound healing. J Biomed Opt. July 2012; 17(7):076016.
Langley R G, Rajadhyaksha M, Dwyer P J, Sober A J, Flotte T J, Anderson R R. Confocal scanning laser microscopy of benign and malignant melanocytic skin lesions in vivo. J Am Acad Dermatol. September 2001; 45(3):365-376.
Leibovitch I, Huilgol S C, Selva D, Richards S, Paver R. Cutaneous squamous carcinoma in situ (Bowen's disease): treatment with Mohs micrographic surgery. J Am AcadDermatol. 2005; 52(6):997-1002.
Lewis-Jones et al., Br J Dermatol. 1995 June; 132(6):942-9.
Lockwood K, Moesgaard S, Yamamoto T, Folkers K. Progress on therapy of breast cancer with vitamin Q10 and the regression of metastases. Biochem Biophys Res Commun. 1995; 212(1):172-7.
Loh et al., JAM ACAD DERMATOL, January 2014.
Marinkovich P M. Epidermolysis Bullosa. Medscape Reference (Drugs, Diseases & Proceducres). 2014.
McKee P, Calonje E, Granter S. Tumors of the surface epithelium. In: Pathology of the Skin. 2. 3rd. London: Elsevier Mosby; 2005:1193-7.
Mackenzie-Wood A, Kossard S, de Launey J, Wilkinson B, Owens M L. Imiquimod 5% cream in the treatment of Bowen's disease. J Am Acad Dermatol. 2001; 44(3):462-70.
McMillan et al. J Invest Dermatol 1998; 110:132-7.
Moreno G, Chia A L, Lim A, Shumack S. Therapeutic options for Bowen's disease. Australas J Dermatol. 2007; 48(1):1-8; quiz 9-10.
Neubert T, Lehmann P. Bowen's disease—a review of newer treatment options. Ther Clin Risk Manag. 2008; 4(5): 1085-95.
Osterberg K A, Wattenberg, L W. Coenzyme-Q Concentration in Proliferative Lesions of Liver. Proc SocExpBiol Med 1961; 108:300
Pearson R W. Studies on the pathogenesis of epidermolysis bullosa. J Invest Dermatol 1962; 39:551-75.
Pearson R W. Clinicopathologic types of epidermolysis bullosa and their nondermatological complications. Arch Dermatol 1988; 124: 718.
Pohla-Gubo G. et al. Dermatol Clin 2010; 28:201-10.
Pope E, Lara-Corrales I, Mellerio J E, Martinez A E, Sibbald C, Sibbald R G. Epidermolysis bullosa and chronic wounds: a model for wound bed preparation of fragile skin. Adv Skin Wound Care. 2013; 26(4): 177-88.
Rajadhyaksha M, Gonzalez S, Zavislan J M, Anderson R R, Webb R H. In vivo confocal scanning laser microscopy of human skin II: advances in instrumentation and comparison with histology. J Invest Dermatol. September 1999; 113(3):293-303.
Reflectance confocal microscopy of cutaneous tumors: an atlas with clinical, dermoscopic and histological correlations: Informa Healthcare; 2008.
Reizner G T, Chuang T Y, Elpern D J, Stone J L, Farmer E R. Bowen's disease (squamous cell carcinoma in situ) in Kauai, Hawaii A population-based incidence report. J Am Acad Dermatol. 1994; 31(4):596-600.
Rusciani L, Proietti I, Rusciani A, et al. Low plasma coenzyme Q10 levels as an independent prognostic factor for melanoma progression J Am Acad Dermatol. 2006; 54(2):234-41.
Sattler E C, Poloczek K, Kastle R, Welzel J. Confocal laser scanning microscopy and optical coherence tomography for the evaluation of the kinetics and quantification of wound healing after fractional laser therapy. J Am Acad Dermatol. October 2013; 69(4):e165-173.
Shannon R L, Strayer D S. Arsenic-induced skin toxicity. Hum Toxicol. 1989; 8(2):99-104.
Schober-Flores, C. Epidermolysis Bullosa: The challenges of wound care. Dermatology Nursing 2003; 15(2): 135-144.
Schober-Flores, C. Epidermolysis Bullosa: A nursing perspective. Dermatology Nursing 1999; 11(4): 243-256.
Straus S M, Kors J A, De Bruin M L, et al. Prolonged QTc interval and risk of sudden cardiac death in a population of older adults. J Am Coll Cardiol. 2006 Jan. 17; 47(2): 362-7.
Sturm H M. Bowen's disease and 5-fluorouracil. J Am Acad Dermatol. 1979; 1(6):513-22.
Tantikun N. Treatment of Bowen's disease of the digit with carbon dioxide laser. J Am Acad Dermatol. 2000; 43(6): 1080-3.
Terhorst D, Maltusch A, Stockfleth E, et al. Reflectance confocal microscopy for the evaluation of acute epidermal wound healing. Wound Repair Regen. November 2011; 19(6):671-679.
Welch M L, Grabski W J, McCollough M L, et al. 5-fluorouracil iontophoretic therapy for Bowen's disease. J Am Acad Dermatol. 1997; 36(6 Pt 1):956-8.
vanEgmond S, Hoedemaker C, Sinclair R. Successful treatment of perianal Bowen's disease with imiquimod. Int J Dermatol. 2007; 46(3):318-9.
Yamashita T, Kuwahara T, Gonzalez S, Takahashi M. Non-invasive visualization of melanin and melanocytes by reflectance-mode confocal microscopy. J Invest Dermatol. January 2005; 124(1):235-240.
Yiasemides E et al. Clin Exp Dermatol 2008; 33:689-97.

The invention claimed is:

1. A method of treating Epidermolysis Bullosa (EB) in a subject having one or more wounds associated with the EB between 2.5 $cm^2$ and 50 $cm^2$ in size, comprising topically administering a pharmaceutical composition comprising a therapeutically effective amount of Coenzyme Q10 (CoQ10) to the subject, thereby reducing the size of the one or more wounds associated with the EB.

2. The method of claim 1, wherein the Epidermolysis Bullosa is Epidermolysis Bullosa Simplex, Junctional Epidermolysis Bullosa, Dystrophic Epidermolysis Bullosa, or Kindler's Syndrome.

3. The method of claim 1, wherein the pharmaceutical composition comprising CoQ10 is administered for a treatment duration from about one week to about twelve weeks.

4. The method of claim 1, wherein the pharmaceutical composition comprising CoQ10 is administered to the subject from 1 to about 14 times per week for the treatment duration.

5. The method of claim 1, wherein the pharmaceutical composition comprising CoQ10 contains from about 1% to about 5% CoQ10 (w/w).

6. The method of claim 1, wherein administering the pharmaceutical composition comprising CoQ10 to the subject provides one or more beneficial effects to the subject, wherein the one or more beneficial effects is selected from the group consisting of:

a. Reduction in pain associated with the EB;

b. Reduction in inflammation associated with the EB;

c. Reduction in the number of blisters and/or wounds associated with the EB;

d. Increase in the rate of healing of one or more blisters and/or wounds associated with the EB;

e. Increase in the structural integrity of the skin of the subject suffering from EB;

f. Reduction in the number of skin infections associated with EB;

g. Increase in wound closure of wounds associated with EB;

h. Increase in re-epithelization of wounds associated with EB;

i. Increase in granulation of wounds associated with EB;

j. Reduction in an epidermal gap distance of a blister and/or wound associated with EB;

k. Reduction in time for blister and/or wound healing associated with EB;

l. Reduction in the amount of concomitant medications administered to the subject in order to treat the subject's EB;

m. Reduction in scarring associated with EB;

n. Increase in keratinocyte production in the skin of the subject; and o. Increase in fibroblast production in the skin of the subject.

7. The method of claim 1, wherein the pharmaceutical composition comprising CoQ10 is administered in the form of a CoQ10 cream at a dosage of CoQ10 between 0.01 $mg/cm^2$ and 5 $mg/cm^2$.

8. The method of claim 1, wherein the pharmaceutical composition comprising CoQ10 is administered with a second composition comprising an additional agent.

9. The method of claim 1, wherein the pharmaceutical composition further comprises an additional agent.

10. The method of claim 1, wherein treatment of the subject results in the reduction of size of one or more blisters and/or wounds by at least about 70% after administration of an effective amount of CoQ10 for a treatment duration of about four weeks.

* * * * *